United States Patent
Yasuda et al.

(10) Patent No.: US 9,435,811 B2
(45) Date of Patent: Sep. 6, 2016

(54) INDUCER OF CHONDROCYTE PROLIFERATION AND DIFFERENTIATION

(75) Inventors: Hisataka Yasuda, Shiga (JP); Yuriko Furuya, Shiga (JP)

(73) Assignee: ORIENTAL YEAST CO., LTD, Tokyo (JP)

( * ) Notice: Subject to any disclaimer, the term of this patent is extended or adjusted under 35 U.S.C. 154(b) by 0 days.

(21) Appl. No.: 12/998,253

(22) PCT Filed: Sep. 9, 2009

(86) PCT No.: PCT/JP2009/066060
§ 371 (c)(1),
(2), (4) Date: Mar. 30, 2011

(87) PCT Pub. No.: WO2010/038610
PCT Pub. Date: Apr. 8, 2010

(65) Prior Publication Data
US 2011/0177069 A1    Jul. 21, 2011

(30) Foreign Application Priority Data

Sep. 30, 2008 (JP) .................... 2008-254153
Dec. 10, 2008 (JP) .................... 2008-314866

(51) Int. Cl.
| | |
|---|---|
| A61K 38/00 | (2006.01) |
| A61K 39/00 | (2006.01) |
| C12N 5/00 | (2006.01) |
| G01N 33/68 | (2006.01) |
| A61K 38/18 | (2006.01) |
| A61K 38/19 | (2006.01) |
| A61K 38/08 | (2006.01) |
| C12N 5/07 | (2010.01) |

(52) U.S. Cl.
CPC ....... *G01N 33/6887* (2013.01); *A61K 38/1841* (2013.01); *A61K 38/1875* (2013.01); *A61K 38/191* (2013.01); *A61K 38/08* (2013.01); *C07K 2319/00* (2013.01); *C12N 5/06* (2013.01); *C12N 2506/00* (2013.01); *G01N 2333/70575* (2013.01); *G01N 2500/10* (2013.01)

(58) Field of Classification Search
CPC .... C12N 5/06; C12N 2506/00; A61K 38/08; C07K 2319/00
USPC ............. 435/377; 424/192.1; 514/16.8, 17.1; 530/300
See application file for complete search history.

(56) References Cited

U.S. PATENT DOCUMENTS

2007/0160594 A1* 7/2007 Filvaroff et al.
2010/0260680 A1* 10/2010 Yasuda et al.

FOREIGN PATENT DOCUMENTS

WO    2008/150025    12/2008

OTHER PUBLICATIONS

Allegrucci et al., 2006, Human Reproduction Update, Vol. Advance Access published on Aug. 26, 2006, p. 1-18.*
Sato et al., 2003, Developmental Biology, vol. 260, p. 404-413.*
Abeyta et al., 2004, Human Molecular Genetics, vol. 13, No. 6, p. 601-608.*
Kolf et al., 2007, Arthritis Research & Therapy, vol. 9, p. 204, 10 pages.*
Hamman et al., 2005, Biodrugs, vol. 19, No. 3, p. 165-177.*
Torchilin et al., 2003, DDT, vol. 8, No. 6, p. 259-266.*
Alenzi et al., 2011, African Journal of Biotechnology, vol. 10(86), pp. 19929-19940.*
Kojima et al., "Subcutaneous injections of a TNF-α antagonistic peptide inhibit both inflammation and bone resorption in collagen-induced murine arthritis," J Med Dent Sci, 2005, vol. 52, pp. 91-99.
Aoki et al., "RANKL/RANK signaling-inhibitor," Nippon Rinsho, Japanese Journal of Clinical Medicine, 2005, vol. 63, No. 9, pp. 1620-1626 (English translation provided).
Kong et al., "Activated T cells regulate bone loss and joint destruction in adjuvant arthritis through oseoprotegerin ligand," Nature, 1999, vol. 402, pp. 304-309.
Nakashima et al., "RANKL and RANK as novel therapeutic targets," Curr Opin Rheumatol, 2003, vol. 15, No. 3, pp. 280-287.
Akama, "RANKL inhibition as therapy for joint damage," Jpn. J. Clin. Immunol., 2007, vol. 30, No. 5, pp. 404-407 (English translation provided).

(Continued)

*Primary Examiner* — Shin Lin Chen
(74) *Attorney, Agent, or Firm* — Hamre, Schumann, Mueller & Larson, P.C.

(57) ABSTRACT

This invention provides a method for administration of an effective amount of RANKL-binding molecules that act on prechondrocytes and/or mesenchymal stem cells, accelerate cartilage differentiation, proliferation, and maturation of such cells, enhance chondrocyte differentiation, and induce chondrocyte proliferation to induce chondrocyte proliferation and differentiation or increase cartilage matrix production and a pharmaceutical composition used for inducing chondrocyte proliferation and differentiation or increasing cartilage matrix production. The pharmaceutical composition used for treatment or prevention of a chondropathies comprises, as an active ingredient, a compound that acts on prechondrocytes and/or mesenchymal stem cells and induces at least one of the following: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix.

4 Claims, 17 Drawing Sheets
(11 of 17 Drawing Sheet(s) Filed in Color)

(56) References Cited

OTHER PUBLICATIONS

Lane et al., "RANKL inhibition with denosumab decreases markers of bone and cartilage turnover in patients with rheumatoid arthritis," Arthritis and Rheumatism, 2006, vol. 54, No. 9, pp. S225-S226.
Kamijo et al., "Amelioration of bone loss in collagen-induced arthritis by neutralizing anti-RANKL monoclonal antibody," Biochem Biophys Res Commun, 2006, vol. 347, pp. 124-132.
Yun et al., "Inducing chondrogenic differentiation in injectable hydrogels embedded with rabbit chondrocytes and growth factor for neocartilage formation," J Biosci Bioeng, 2008, vol. 105, No. 2, pp. 122-126.
Takemura et al., "Involvement of OPG in arthritic disorder," Molecular Rheumatism, 2007, vol. 4, No. 2, pp. 23-28 (English translation provided).
Redlich et al., "Osteoclasts are essential for TNF-α-mediated joint destruction," The Journal of Clinical Investigation, 2002, vol. 110, No. 10, pp. 1419-1427.
Aoki et al., "A TNF receptor loop peptide mimic blocks RANK ligand-induced signaling, one resorption, and bone loss," The Journal of Clinical Investigation, 2006, vol. 116, No. 6, pp. 1525-1534.
Saito et al., "A tumor necrosis factor receptor loop peptide mimic inhibits bone destruction to the same extent as anti-tumor necrosis factor monoclonal antibody in murine collagen-induced arthritis," Arthritis & Rheumatism, 2007, vol. 56, No. 4, pp. 1164-1174.
Yang et al., "cAMP/PKA regulates osteogenesis, adipogenesis and ratio of RANKL/OPG mRNA expression in mesenchymal stem cells by surpressing leptin," PLoS ONE, 2008, vol. 3, issue 2, 10 pages total.
Suzuki et al., "A tumor necrosis factor-alpha antagonist inhibits inflammatory bone resorption induced by Porphyromonas gingivalis infection in mice," Journal of Periodontal Research, 2006, vol. 41, No. 2, pp. 81-91.
Sitcheran et al., "NF-κB mediates inhibition of mesenchymal cell differentiation through a posttranscriptional gene silencing mechanism," Genes & Development, 2003, vol. 17, pp. 2368-2373.
Aizawa et al., "Induction of apoptosis in chondrocytes by tumor necrosis factor-alpha," Journal of Orthopaedic Research, 2001, vol. 19, pp. 785-796.

\* cited by examiner

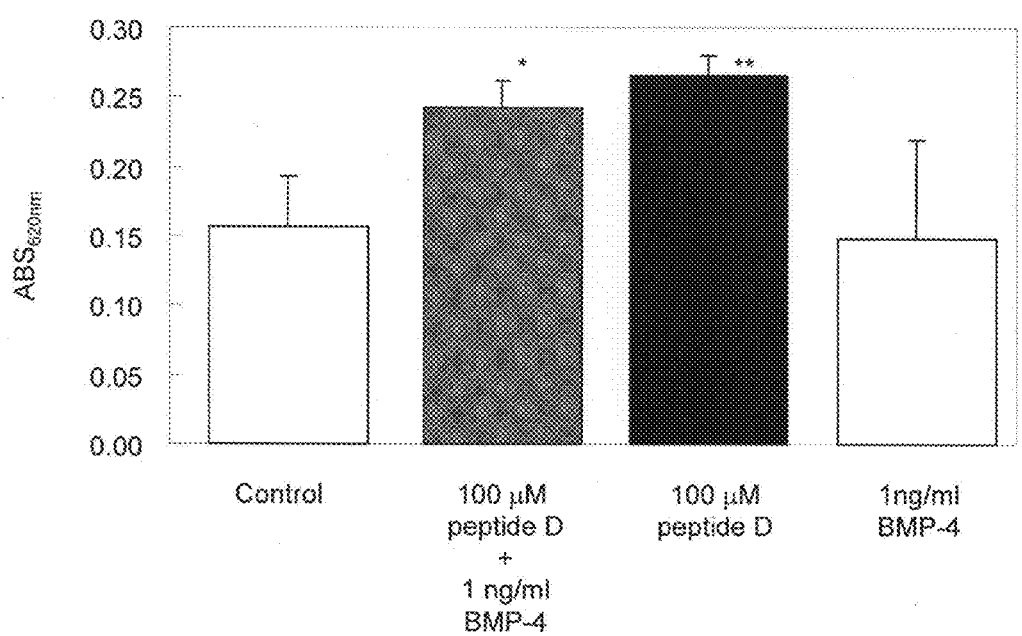

C: control, D: peptide D, B: BMP-4

C: Control, D: peptide D, B: BMP-4

INDUCER OF CHONDROCYTE PROLIFERATION AND DIFFERENTIATION

TECHNICAL FIELD

The present invention relates to an inducer of chondrocyte proliferation and differentiation or an agent for increasing cartilage matrix production stimulating chondrogenesis, which comprises RANKL-binding molecules that accelerate differentiation and maturation of prechondrocytes and/or mesenchymal stem cells. The present invention also relates to a method of using the inducer to differentiate prechondrocytes and/or mesenchymal stem cells or to increase cartilage matrix production. Further, the present invention relates to a method for screening for a substance that binds to and transmits a signal to RANKL to differentiate and proliferate prechondrocytes and/or mesenchymal stem cells or a substance that increases cartilage matrix production, the substance obtained by such screening method, and a pharmaceutical composition comprising the obtained substance.

BACKGROUND ART

Cartilage is composed of chondrocytes and a large quantity of intercellular cartilage matrices. Cartilage is classified into three types based on differences in cartilage matrix properties: i.e., hyaline cartilage constituting skeletal primordias at the fetal stage or major parts of articular cartilage; fibrocartilage comprising type I collagen in the matrix; and elastic cartilage existing in the auricula and in the epiglottis (see *Shih Hone no Kagaku* (Bone Biology), written and edited by Tateo Suda et al., Ishiyaku Pub, Inc. and *KouSoshiki Kenkyu Handbook* (Handbook of Hard Tissue Research), Division of Hard Tissue Research, Graduate School, Matsumoto Dental University).

Chondrocytes as constituents originate from pluripotent undifferentiated mesenchymal stem cells, and undifferentiated mesenchymal stem cells are aggregated by the Sox transcription factor (SRY-related HMG box-containing gene) 9 and converted into prechondrocytes. The prechondrocytes secrete a group of matrices such as type II collagen, type IX collagen, and proteoglycan to be converted into cartilage matrices. Consequently cartilage matrices increase, cells are individualized, and differentiated into chondroblasts through synergistic action with transcription factors such as Sox5 and Sox6. Further, transcription factor expression (i.e., of the runt-related gene 2 (Runx2)) is suppressed and expression of ERG/C-1-1 (i.e., the ets related gene) is accelerated in immature chondroblasts, and differentiation into permanent chondrocytes advances (see *Hone/nankotsu taisha to chumoku no hone shikkan* (Bone/cartilage metabolism and critical bone diseases), Toshio Matsumoto (ed.), Yodosha Co., Ltd. and Inada et al., Dev. Dyn 214: 279, 1999). It was reported that enlarged chondrocytes would lead to enhanced expression of type X collagen.

There are two patterns for the processes of cartilage growth. One of them is interstitial growth, in which cells differentiated, into chondrocytes and surrounded by the cartilage matrix proliferate through cell division. Each chondrocyte secretes a matrix, and cartilage tissue is then enlarged.

The other growth pattern is appositional growth caused by the perichondrium. Cartilage tissue is covered with a perichondrium except for the articular surface of the articular cartilage. The strong perichondrium is constituted of fibroblasts, but is similar to chondrocytes in the inner layer, thus the difference between fibroblasts and chondrocytes is unclear. Perichondrium cells in the inner layer proliferate while gradually changing into circular forms, and such cells further a secrete cartilage matrix and grow outwardly.

In general, the outside of the perichondrium of the cartilage tissue is in contact with connective tissue that is rich in blood vessels and nerves, although the inside thereof does not contain blood vessels or nerves. When the cartilage is damaged inside, accordingly, it cannot be repaired by undifferentiated stem cells, cytokines, and so on. In addition, the capacity of the chondrocytes for mitotic proliferation is poor, and self-repair of chondrocytes is very difficult.

The method to repair a articular cartilage is a topical injection in cartilage matrix, a implantation of cultured bone marrow mesenchymal stem cells to prepare autologous chondrocytes, or an impregnating of matrix disc with chondrocyte growth factors. Transforming growth factor (TGF-β1), insulin-like growth factor (IGF-1), basic fibroblast growth factor (bFGF), PTH-related peptide (PTHrP) that are highly homologous to the 13 N-terminal amino acids of PTH, hepatocyte growth factor (HGF), and bone morphogenetic protein (BMP) belonging to TGF-β superfamily have been reported as chondrocyte growth factors. BMP and TGF-β may induce to lose the function of chondrocytes after implantation due to calcification in article cartilage, because these factors have some important effects, such as aggregation of undifferentiated mesenchymal stem cells, and inhibitory effect on terminal chondrocytic differentiation in addition to the effect on chondrocyte growth.

Osteoclast differentiation factor (i.e., the receptor activator of NF-κB ligand (RANKL)) is a membrane-binding protein of tumor necrosis factor (TNF) family that is induced on osteoblasts/stromal cells by bone resorption factors, and is necessary for differentiation and maturation of osteoclasts (see Yasuda et al., Proc. Natl. Acad. Sci., U.S.A., 95: 3597, 1998 and Lacey et al., Cell 93: 165, 1998). Research focusing on RANKL/RANK/OPG, including a receptor (i.e., the receptor activator of NF-κB (RANK)) and a decoy receptor (i.e., the osteoprotegerin (OPG)), has led to elucidation of the control mechanism for osteoclast differentiation and maturation in vivo, and the correlation between these 3 molecules and metabolic bone diseases has also become elucidated (see Suda et al., Endocr Rev, 20: 345, 1999).

A correlation between RANKL and differentiation and proliferation of prechondrocytes and/or mesenchymal stem cells has been unknown.

DISCLOSURE OF THE INVENTION

The present invention is intended to provide a method for inducing chondrocyte proliferation, and differentiation or increasing cartilage matrix production via administration of an effective amount of molecules that have capacity of binding to RANKL, act on prechondrocytes and/or mesenchymal stem cells, accelerate chondrocytes differentiation, proliferation, and maturation of these cells, enhance chondrocyte differentiation, and induce chondrocyte proliferation. The present invention is also intended to provide a pharmaceutical composition including the molecules used for inducing chondrocyte proliferation and differentiation or for increasing cartilage matrix production.

The present inventors discovered that a variety of proteins, peptides, peptoids, and molecules that act on RANKL induced proliferation and differentiation of chondrocytes or acceleration of cartilage matrix production from prechondrocytes and/or mesenchymal stem cells. Specifically, the present invention is as follows.

[1] A pharmaceutical composition used for treatment or prevention of chondropathies comprising, as an active ingredient, a compound that acts on prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation.

[2] The pharmaceutical composition used for treatment or prevention of chondropathies according to [1], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation acts on RANKL in the prechondrocytes and/or mesenchymal stem cells.

[3] The pharmaceutical composition used for treatment or prevention of chondropathies according to [1], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a compound selected from the group consisting of RANK, a mutant or a fragment peptide of RANK, a peptide structurally similar to RANK, a peptide structurally similar to a fragment peptide of RANK, a chemical substance structurally similar to RANK, a chemical substance structurally similar to a fragment peptide of RANK, OPG, a mutant or a fragment peptide of OPG, a peptide structurally similar to OPG, a peptide structurally similar to a fragment peptide of OPG, a chemical substance structurally similar to OPG, and a chemical substance structurally similar to a fragment peptide of OPG.

[4] The pharmaceutical composition used for treatment or prevention of chondropathies according to [2], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a compound selected from the group consisting of RANK, a mutant or a fragment peptide of RANK capable of acting on RANKL, a peptide structurally similar to RANK and capable of acting on RANKL, a peptide structurally similar to a fragment peptide of RANK and capable of acting on RANKL, a chemical substance structurally similar to RANK and capable of acting on RANKL, a chemical substance structurally similar to a fragment peptide of RANK and capable of acting on RANKL, OPG, a mutant or a fragment peptide of OPG capable of acting on RANKL, a peptide structurally similar to OPG and capable of acting on RANKL, a peptide structurally similar to a fragment peptide of OPG and capable of acting on RANKL, a chemical substance structurally similar to OPG and capable of acting on RANKL, and a chemical substance structurally similar to a fragment peptide of OPG capable of acting on RANKL.

[5] The pharmaceutical composition used for treatment or prevention of chondropathies according to [1] or [2], wherein the compound that acts on the chondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a peptide comprising the amino acid sequence as shown in SEQ ID NO: 7 or a salt thereof.

[6] The pharmaceutical composition used for treatment or prevention of chondropathies according to [1] or [2], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a fusion protein of a peptide comprising the amino acid sequence as shown in SEQ ID NO: 7 or a salt thereof and Flag represented by the amino acid sequence DYKDDDDK (SEQ ID NO: 16) or DYLDDDDL (SEQ ID NO: 17), GST, or an Fc region of IgG.

[7] The pharmaceutical composition used for treatment or prevention of chondropathies according to [1] or [2], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is an anti-RANKL antibody or a functional fragment thereof.

[8] The pharmaceutical composition used for treatment or prevention of chondropathies according to any one of [1] to [7] comprising, as an active ingredient, a compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix.

[9] An inducer of chondrocyte proliferation and differentiation comprising, as an active ingredient, a compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation.

[10] The inducer of chondrocyte proliferation and differentiation according to [9], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation acts on RANKL in the prechondrocytes and/or mesenchymal stem cells.

[11] The inducer of chondrocyte proliferation and differentiation according to [9], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a compound selected from the group consisting of RANK, a mutant or a fragment peptide of RANK, a peptide structurally similar to RANK, a peptide structurally similar to a fragment peptide of RANK, a chemical substance structurally similar to RANK, a chemical substance structurally similar to a fragment peptide of RANK, OPG, a mutant or a fragment peptide of OPG, a peptide structurally similar to OPG, a peptide structurally similar to a fragment peptide of OPG, a chemical substance structurally similar to OPG, and a chemical substance structurally similar to a fragment peptide of OPG.

[12] The inducer of chondrocyte proliferation and differentiation according to [10], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a compound selected from the group consisting of RANK, a mutant or a fragment peptide of RANK capable of acting on RANKL, a peptide structurally similar to RANK and capable of acting on RANKL, a peptide structurally similar to a fragment peptide of RANK and capable of acting on RANKL, a chemical substance structurally similar to RANK and capable of acting on RANKL, a chemical substance structurally similar to a fragment peptide of RANK capable of acting on RANKL, OPG, a mutant or a fragment peptide of OPG capable of acting on RANKL, a peptide structurally similar to OPG and capable of acting on RANKL, a peptide structurally similar to a fragment peptide of OPG and capable of acting on RANKL, a chemical substance structurally similar to OPG and capable of acting on RANKL, and a chemical substance structurally similar to a fragment peptide of OPG capable of acting on RANKL.

[13] The inducer of chondrocyte proliferation and differentiation according to [9] or [10], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a peptide comprising the amino acid sequence as shown in SEQ ID NO: 7 or a salt thereof.

[14] The inducer of chondrocyte proliferation and differentiation according to [9] or [10], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is a fusion protein of a peptide comprising the amino acid sequence as shown in SEQ ID NO: 7 or a salt thereof and Flag represented by the amino acid sequence DYKDDDDK (SEQ ID NO: 16) or DYLDDDDL (SEQ ID NO: 17), GST, or an Fc region of IgG.

[15] The inducer of chondrocyte proliferation and differentiation according to [9] or [10], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation is an anti-RANKL antibody or a functional fragment thereof.

[16] An agent for increasing cartilage matrix production comprising, as an active ingredient, a compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix.

[17] The agent for increasing cartilage matrix production according to [16], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix acts on RANKL in the prechondrocytes and/or mesenchymal stem cells.

[18] The agent for increasing cartilage matrix production according to [16], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix is a compound selected from the group consisting of RANK, a mutant or a fragment peptide of RANK, a peptide structurally similar to RANK, a peptide structurally similar to a fragment peptide of RANK, a chemical substance structurally similar to RANK, a chemical substance structurally similar to a fragment peptide of RANK, OPG, a mutant or a fragment peptide of OPG, a peptide structurally similar to OPG, a peptide structurally similar to a fragment peptide of OPG, a chemical substance structurally similar to OPG, and a chemical substance structurally similar to a fragment peptide of OPG.

[19] The agent for increasing cartilage matrix production according to [17], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix is a compound selected from the group consisting of RANK, a mutant or a fragment peptide of RANK capable of acting on RANKL, a peptide structurally similar to RANK and capable of acting on RANKL, a peptide structurally similar to a fragment peptide of RANK and capable of acting on RANKL, a chemical substance structurally similar to RANK and capable of acting on RANKL, a chemical substance structurally similar to a fragment peptide of RANK capable of acting on RANKL, OPG, a mutant or a fragment peptide of OPG capable of acting on RANKL, a peptide structurally similar to OPG and capable of acting on RANKL, a peptide structurally similar to a fragment peptide of OPG and capable of acting on RANKL, a chemical substance structurally similar to OPG and capable of acting on RANKL, and a chemical substance structurally similar to a fragment peptide of OPG capable of acting on RANKL.

[20] The agent for increasing cartilage matrix production according to [16] or [17], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix is a peptide comprising the amino acid sequence as shown in SEQ ID NO: 7 or a salt thereof.

[21] The agent for increasing cartilage matrix production according to [16] or [17], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix is a fusion protein of a peptide comprising the amino acid sequence as shown in SEQ ID NO: 7 or a salt thereof and Flag represented by the amino acid sequence DYKDDDDK (SEQ ID NO: 16) or DYLDDDDL (SEQ ID NO: 17), GST, or an Fc region of IgG.

[22] The agent for increasing cartilage matrix production according to [16] or [17], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix is an anti-RANKL antibody or a functional fragment thereof.

[23] A pharmaceutical composition used for treatment or prevention of chondropathies comprising, as an active ingredient, a peptide comprising the amino acid sequence as shown in SEQ ID NO: 7 or a salt thereof.

[24] A pharmaceutical composition used for treatment or prevention of chondropathies comprising, as an active ingredient, a fusion protein of a peptide comprising the amino acid sequence as shown in SEQ ID NO: 7 or a salt thereof and Flag represented by the amino acid sequence DYKDDDDK (SEQ ID NO: 16) or DYLDDDDL (SEQ ID NO: 17), GST, or an Fc region of IgG.

[25] The pharmaceutical composition used for treatment or prevention of chondropathies according to [23] or [24], wherein the cartilage disease is selected from the group consisting of cartilage defect, osteochondritis dissecans, articular rheumatism, osteoarthritis, congenital cartilage disease, and cartilage injury.

[26] A method for screening for a compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation,
the method comprising, when a candidate compound is brought into contact with RANKL-expressing prechondrocytes and/or mesenchymal stem cells and the candidate compound accelerates differentiation or proliferation of cells capable of differentiating into chondrocytes, determining that the candidate compound acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation.

[27] The screening method according to [26], wherein the compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; and (e) chondrocyte proliferation acts on RANKL in the prechondrocytes and/or mesenchymal stem cells.

[28] The screening method according to [26] or [27], which screens for a compound that acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix,
the method comprising, when a candidate compound is brought into contact with RANKL-expressing prechondrocytes and/or mesenchymal stem cells and the candidate compound accelerates differentiation or proliferation of cells capable of differentiating into chondrocytes, determining that the candidate compound acts on the prechondrocytes and/or mesenchymal stem cells and induces at least one of: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix.

[29] The pharmaceutical composition according to any one of [1] to [8], which further comprises at least one protein belonging to the TGF-β superfamily.

[30] The pharmaceutical composition according to [29], wherein the protein belonging to the TGF-β superfamily is TGF-β3 and/or BMP-2.

[31] The inducer of chondrocyte proliferation and differentiation according to any one of [9] to [15], which further comprises at least one protein belonging to the TGF-β superfamily.

[32] The inducer of chondrocyte proliferation and differentiation according to [31], wherein the protein belonging to the TGF-β superfamily is TGF-β3 and/or BMP-2.

[33] The agent for increasing cartilage matrix production according to any one of [16] to [22], which further comprises at least one protein belonging to the TGF-β superfamily.

[34] The agent for increasing cartilage matrix production according to [33], wherein the protein belonging to the TGF-β superfamily is TGF-β3 and/or BMP-2.

[35] The pharmaceutical composition according to any one of [23] to [25], which further comprises at least one protein belonging to the TGF-β superfamily.

[36] The pharmaceutical composition according to [35], wherein the protein belonging to the TGF-β superfamily is TGF-β3 and/or BMP-2.

This description includes part or all of the contents as disclosed in the descriptions and/or drawings of Japanese Patent Application Nos. 2008-254153 and 2008-314866, which are priority documents of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1B is a chart showing the absorbance data of acceleration of chondrocyte differentiation from human mesenchymal stem cells treated with peptide D by eluting a pigment from alcian-blue-stained cells.

PREFERRED EMBODIMENTS OF THE INVENTION

Figure 1A:
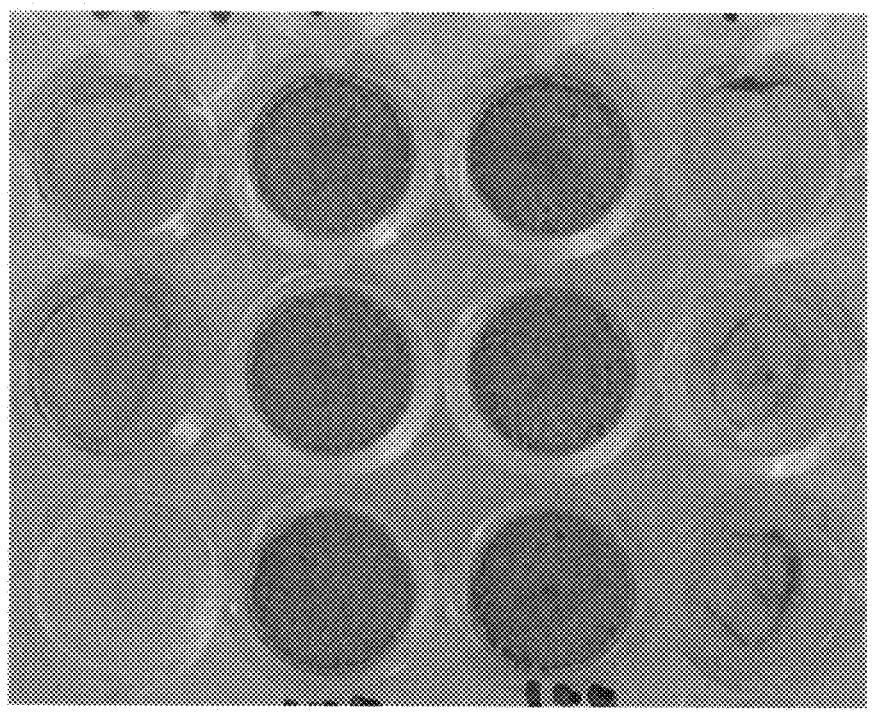
FIG. 1A is a photograph showing induction of chondrocyte differentiation from human mesenchymal stem cells with peptide D with alcian blue staining.

Hereafter, the present invention is described in detail.

RANKL (i.e., the receptor activator of NF-κB ligand) is a ligand of RANK (i.e., the receptor activator of NF-κB), which is a member of the TNF superfamily, and it is a type 2 transmembrane protein constituted an intracellular domain (a domain comprising amino acids 1 to 48 from the N-terminus of RANKL), a transmembrane domain, and an extracellular domain (JP Patent Publication (kohyo) No. 2002-509430 A; International Publication No. WO 98/46644 (currently U.S. Pat. No. 3,523,650). RANKL expressed on osteoblasts and osteoblastic progenitor cells by bone resorption factors. Osteoblastic progenitor cells indicated all cells capable of differentiating into osteoblasts. These cells are prechondrocytes, preosteoblastic cells, mesenchymal stem cells, interstitial cells, and myoblasts, which are capable of differentiating into osteoblasts. An extracelluar domain after 152 amino acids from the N-terminal site is the TNF ligand family homologous domain. SEQ ID NOs: 1 and 2 each show the full-length nucleotide sequence and amino acid sequence of human RANKL. SEQ ID NOs: 3 and 4 each show the full-length nucleotide sequence and amino acid sequence of RANK.

OPG (i.e., the osteoprotegerin) is a protein structurally similar to RANK and it is capable of acting on RANKL. SEQ ID NOs: 5 and 6 each show the full-length nucleotide sequence and amino acid sequence of OPG.

The present invention concerns a pharmaceutical composition containing an active ingredient, that is a compound acts on the prechondrocytes and/or mesenchymal stem cells and accelerate cartilage differentiation, proliferation, and maturation of such cells, enhance chondrocyte differentiation, induces chondrocyte proliferation, or increases cartilage matrix production; specifically, a compound that act on the prechondrocytes and/or mesenchymal stem cells and induces at least 1, 2, 3, 4, or all of the following: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix. Combinations of two or more of (a) to (f)

are (a) and (b); (a) and (c); (a) and (d); (a) and (e); (a) and (f); (b) and (c); (b) and (d); (b) and (e); (b) and (f); (c) and (d); (c) and (e); (c) and (f); (d) and (e); (d) and (f); (e) and (f); (a), (b), and (c); (a), (b), and (d); (a), (b), and (e); (a), (b), and (f); (a), (c), and (d); (a), (c), and (e); (a), (c), and (f); (a), (d), and (e); (a), (d), and (f); (a), (e), and (f); (a), (b), (c), and (d); (a), (b), (c), and (e); (a), (b), (c), and (f); (a), (b), (d), and (e); (a), (b), (d), and (f); (a), (b), (e), and (f); (a), (c), (d), and (e); (a), (c), (d), and (f); (a), (c), (e), and (f); (a), (d), (e), and (f); (b), (c), (d), and (e); (b), (c), (d), and (f); (b), (c), (e), and (f); (b), (d), (e), and (f); (c), (d), (e), and (f); (a), (b), (c), (d), and (e); (a), (b), (c), (d), and (f); (a), (b), (c), (e), and (f); (a), (b), (d), (e), and (f); (a), (c), (d), (e), and (f); (b), (c), (d), (e), and (f); and (a), (b), (c), (d), (e), and (f). An example of such pharmaceutical composition is a pharmaceutical composition containing an active ingredient, that is a compound acts on the prechondrocytes and/or mesenchymal stem cells and accelerates cartilage differentiation, proliferation, and maturation of such cells, enhances chondrocyte differentiation, induces cartilage proliferation, or increases cartilage matrix production. An example of an active ingredient is a compound that acts on RANKL, transmits a signal to the prechondrocytes and/or mesenchymal stem cells, and accelerates differentiation, proliferation, and maturation of such cells, enhances chondrocyte differentiation, induces chondrocyte proliferation, or increases cartilage matrix production. When such compounds acts on RANKL, the animal origin of RANKL on which such compounds can act is not limited, and RANKL with any animal origin, such as human RANKL, mouse RANKL, or rat RANKL, can be targeted. The term "[compound] acts on RANKL" used herein refers to a situation in which a compound acts on RANKL and transmits a signal to the prechondrocytes and/or mesenchymal stem cells. For example, a compound may bind to RANKL and transmit a signal to prechondrocytes and/or mesenchymal stem cells.

A compound that acts on RANKL, acts on the prechondrocytes and/or mesenchymal stem cells, and accelerates differentiation, proliferation, and maturation of such cells, enhances chondrocyte differentiation, induces chondrocyte proliferation, or increases cartilage matrix production may be any compound that acts on RANKL originating from any animal species. Examples of such compounds include a natural peptide, non-natural peptide, chemically-synthesized compound, or low-molecular-weight compounds derived from microorganism.

Examples of the compound indicated the present invention, which acts on the prechondrocytes and/or mesenchymal stem cells and accelerates differentiation, proliferation, and maturation of such cells, enhances chondrocyte differentiation, induces chondrocyte proliferation, or increases cartilage matrix production include a mutant or a fragment peptide of RANK, a peptide structurally similar to RANK, a peptide structurally similar to a fragment peptide of RANK, a chemical substance structurally similar to RANK, and a chemical substance structurally similar to a fragment peptide of RANK. Examples of these compound include RANK, a mutant or a fragment peptide of RANK capable of acting on RANKL, a peptide structurally similar to RANK and capable of acting on RANKL, a peptide structurally similar to a fragment peptide of RANK and capable of acting on RANKL, a chemical substance structurally similar to RANK and capable of acting on RANKL, and a chemical substance structurally similar to a fragment peptide of RANK capable of acting on RANKL.

The term "chemical substance" refers to a compound is except for a peptide or protein. RANK contains membrane RANK or soluble RANK. The term "membrane RANK" refers to RANK having a transmembrane region bound to a cell surface, and using a cell expressing natural RANK or a mammalian cell expressed recombinant RANK, or RANKFc. RANKFc is a fusion protein composing of an extracellular region of human RANK with a Fc region of human IgG (i.e., an Fc fusion protein).

According to the present invention, the term "structurally similarity" refers to similarity of partial structural conformations, capable of acting on RANKL, for example. Generally, a protein or peptide constituted the similar primary structure represented by an amino acid sequence, and a compound composed of a different amino acid sequence having a similar conformation and capable of acting on RANKL are included.

Further examples of compounds that act on prechondrocytes and/or mesenchymal stem cells and accelerate differentiation, proliferation, and maturation of such cells, enhance chondrocyte differentiation, induce chondrocyte proliferation, or increase cartilage matrix production include OPG, a mutant or a fragment peptide of OPG, a peptide structurally similar to OPG, a peptide structurally similar to a fragment peptide of OPG, a chemical substance structurally similar to OPG, and a chemical substance structurally similar to a fragment peptide of OPG. Examples of compounds that act on RANKL, act on the prechondrocytes and/or mesenchymal stem cells, and accelerate differentiation, proliferation, and maturation of such cells, enhance chondrocyte differentiation, induce chondrocyte proliferation, or increase cartilage matrix production include OPG, a mutant or a fragment peptide of OPG capable of acting on RANKL, a peptide structurally similar to OPG and capable of acting on RANKL, a peptide structurally similar to a fragment peptide of OPG and capable of acting on RANKL, a chemical substance structurally similar to OPG and capable of acting on RANKL, and a chemical substance structurally similar to a fragment peptide of OPG capable of acting on RANKL.

The term "chemical substance" refers to a compound except for a peptide or protein. OPG contains membrane OPG or soluble OPG. The term "membrane OPG" refers to OPG expressed on cell surface to bind at the C-terminal region or the like. Cells expressing natural OPG, mammalian cells expressing recombinant OPG, or OPGFc can be used. OPGFc is a fusion protein of OPG with a Fc region of human IgG (i.e., an Fc fusion protein).

An example of an RANK or OPG analog includes a protein or a peptide comprising one or several point mutations of the amino acid sequence or a fragment peptide derived from RANK or OPG by deletion, substitution, or addition of amino acids and having the activity of RANK or OPG. The term "one or several" refers to 1 to 9, preferably 1 to 5, and more preferably 1 or 2.

An example of a peptide of RANK having a structure similar to that of a region binding to RANKL is a peptide comprising the amino acid sequence represented by SEQ ID NO: 7 (i.e., peptide D). This peptide is a cyclic peptide comprising a Cys 2-Cys 8 disulfide bond.

Further, a peptide salt of RANK having a structure similar to that of a region binding to RANKL can also be used. A peptide salt is not particularly limited, provided that it is pharmaceutically acceptable. Examples of peptide salts include acid addition salts and base addition salts. Examples of acid addition salts include organic acid salts, such as acetic acid salt, malic acid salt, succinic acid salt, trifluoroacetic acid (TFA) salt, tartaric acid salt, or citric acid salt and inorganic acid salts, such as hydrochloric acid salt, sulfuric acid salt, nitric acid salt, or phosphoric acid salt. Examples of base addition salts include alkali metals salt, such as sodium salt or potassium salt, alkaline earth metals salt, such as calcium salt or magnesium salt, and amines salt, such as ammonium salt or triethylamine salt. Among them, acetic acid salt is preferable, and acetic acid salt of the peptide comprising the amino acid sequence shown in SEQ ID NO: 7 is particularly preferable.

In addition, a fusion protein of a peptide having a structure similar to RANK capable of binding to RANKL with GST (glutathione-S-transferase) or a Fc region of human IgG (i.e., the GST fusion protein or the Fc fusion protein) can also be used. An example of such fusion protein is a fusion protein of peptide D with Flag represented by the amino acid sequence DYKDDDDK (SEQ ID NO: 16) or DYLDDDDL (SEQ ID NO: 17), GST (glutathione-S-transferase), or a Fc region of human IgG (i.e., the Flag fusion peptide D, the Fc fusion peptide D, or the GST fusion peptide D). Such fusion protein exhibits improved stability in vivo and its longer half-life in the blood. A fusion protein of GST or a fusion protein of Fc with other epitope tag can also be used. Examples of other epitope tag include a polyhistidine tag comprising 2 to 12, preferably 4 or more, more preferably 4 to 7, and further preferably 5 or 6 histidines, a FLAG tag, an Myc tag, a V5 tag, an Xpress tag, an HQ tag, an HA tag, an AU1 tag, a T7 tag, a VSV-G tag, a DDDDK tag, an S tag, a CruzTag09, a CruzTag22, a CruzTag41, a Glu-Glu tag, an Ha.11 tag, a KT3 tag, thioredoxin, a maltose-binding protein (MBP), and β galactosidase.

In the present invention, a compound that acts on RANKL, acts on the prechondrocytes and/or mesenchymal stem cells, and accelerates differentiation, proliferation, and maturation of such cells, enhances chondrocyte differentiation, induces chondrocyte proliferation, or increases cartilage matrix production is occasionally referred to as an agonist to RANKL.

In addition, such compounds contain an anti-RANKL antibody or a functional fragment antibody that acts on RANKL on the prechondrocytes and/or mesenchymal stem cells, and accelerates differentiation, proliferation, and maturation of such cells, enhances chondrocyte differentiation, induces chondrocyte proliferation, or increases cartilage matrix production. In the present invention, such an antibody is occasionally referred to as an agonist antibody to RANKL. An anti-RANKL antibody can be obtained as a polyclonal or monoclonal antibody by a known technique, with a monoclonal antibody being preferable. Examples of a monoclonal antibody include a monoclonal antibody produced by a hybridoma and a monoclonal antibody produced by a host that has been transformed by genetic engineering procedures with the use of an expression vector comprising the antibody gene. A monoclonal antibody-producing hybridoma can be produced by a known method as described below. Specifically, such hybridoma can be produced by carrying out immunization with the use of membrane-bound or soluble RANKL or a RANKL fragment peptide as a sensitized antigen by a known immunization method, fusing the resulting immunized cell with a known parent cell by a general cell fusion method, and screening for a monoclonal-antibody-producing cell by a known screening method. Upon immunization with RANKL, RANKL may be allowed to bind to a carrier protein such as bovine serum albumin (BSA), keyhole lympet haemocyanin, or the like before use. A monoclonal antibody that can be used is a recombinant monoclonal antibody produced by cloning the antibody gene with the use of a hybridoma, incorporating the cloned gene into an appropriate vector, and introducing the vector into a host by the gene recombinant technique (e.g., see Vandamme, A. M. et al., Eur. J. Biochem. 1990; 192: 767-775). In such case, it is possible to separately incorporate DNAs encoding the antibody heavy chain (H chain) and the light chain (L chain) into expression vectors for simultaneous transformation of a host cell. Alternatively, it is possible to incorporate DNA encoding the H chain and the L chain into a single expression vector for transformation of a host cell (see WO 94/11523). Also, it is possible to produce a recombinant antibody with the use of a transgenic animal. For instance, a fusion gene may be prepared by inserting the antibody gene into a non-terminal region of the gene encoding a protein peculiarly produced in milk (e.g., goat β-casein). A DNA fragment comprising the fusion gene into which the antibody gene has been inserted is injected into a goat embryo and the thus obtained embryo is introduced into a female goat. A desired antibody can be obtained from milk produced by a transgenic goat born from the goat into which the embryo had been introduced or by a progeny thereof (Ebert, K. M. et al., Bio/Technology 1994; 12: 699-702).

Examples of the anti-RANKL antibody of the present invention include a recombinant antibody that have been artificially modified so as to have reduced heteroantigenicity against humans, such as a chimeric antibody, a humanized antibody, and a human antibody, which can be produced by known methods. A chimeric antibody can be obtained by getting DNA encoding the antibody V region, ligating the DNA to DNA encoding the human antibody C region, incorporating the resultant into an expression vector, and introducing the vector into a host for antibody production. A humanized antibody is referred to as reconstituted (re-shaped) human antibody in some cases. A humanized antibody is obtained by transplanting the complementary determining region (CDR) of a non-human mammal antibody such as a mouse antibody into the complementary determining region of a human antibody. It can be produced by known methods (see EP 125023 and WO96/02576). The C-region of a chimeric antibody and that of a humanized antibody are used as the C region of a chimeric antibody and of a humanized antibody, respectively, and a Cγ1, Cγ2, Cγ3, or Cγ4 H chain and a Cκ or Cλ L chain can be used, for example. Further, in order to improve the stability of an antibody or production stability, the human antibody C region may be modified.

A human antibody can be obtained by administering an antigen to a transgenic animal having the ability to produce a human-derived antibody that has been imparted via introduction of, for example, a human antibody gene locus. An example of such transgenic animal is a mouse, and a method for preparing a mouse capable of producing a human antibody is described in, for example, WO 02/43478.

The term "anti-RANKL antibody" includes not only a complete antibody but also a functional fragment of an antibody. A functional fragment of an antibody corresponds to a part of an antibody (i.e., a partial fragment) having at least one action of the antibody on a relevant antigen. Specific examples thereof include F (ab')$_2$, Fab', Fab, Fv, disulfide-bound Fv, single chain Fv (scFv), and a polymer thereof (D. J. King, Applications and Engineering of Monoclonal Antibodies, 1998, T. J. International Ltd.).

In addition, when a monoclonal antibody is used, a single type of monoclonal antibody may be used alone. Two or more types, for example, 2, 3, 4, or 5 types of monoclonal antibodies each recognizing a different epitope, may be used.

It is possible to determine whether or not the above compound has agonist activity that promotes signal transmission through RANKL, for example, administering an antibody to prechondrocytes and/or mesenchymal stem cells capable of expressing RANKL, allowing the antibody to act on RANKL, and examining if differentiation, proliferation, or generation of cartilage, or increase cartilage matrix production. Differentiation and proliferation can be determined using the elevated expression level of the α1 chain of type II collagen in the cell, for example. Since the cartilage matrix is stained alcian blue, whether or not the cartilage is generated and cartilage matrix production is increased can be determined by alcian blue staining.

Furthermore the present invention concerns a pharmaceutical composition comprising a compound that acts on the prechondrocytes and/or mesenchymal stem cells and accelerates cartilage differentiation, proliferation, and maturation of such cells, enhances chondrocyte differentiation, induces chondrocyte proliferation, or increases cartilage matrix production; i.e., a compound that acts on the prechondrocytes and/or mesenchymal stem cells and induces at least 1, 2, 3, 4, or all of the following: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix in combination with at least one protein belonging to the TGF-β superfamily. Administration of such compound in combination with at least one protein belonging to the TGF-β superfamily can lead synergistic effects on: (a) acceleration of prechondrocyte and/or mesenchymal stem cell differentiation; (b) acceleration of prechondrocyte and/or mesenchymal stem cell proliferation; (c) acceleration of prechondrocyte and/or mesenchymal stem cell maturation; (d) enhancement of chondrocyte differentiation; (e) chondrocyte proliferation; and (f) increased production of the cartilage matrix or effects of increasing cartilage matrix production.

Examples of proteins belonging to the TGF-β superfamily indicate the BMP family including BMP2, 4, 7, the growth and differentiation factors (GDF)-5, 6, and 7, and the TGF family including activin, inhibin, TGF-α, TGF-β1 to β3, and the latent transforming growth factor protein (LTBP) (Bilezilian et al., Principles of Bone Biology, Third Edition, Chapter 53). Several ones of these factors can be used in combination. For example, the above compound can be used in combination with TGF-β3 and/or BMP-2.

The composition of the present invention being capable of enhancing chondrogenesis or increasing cartilage matrix production can be used as a research reagent in vitro, and a pharmaceutical composition in vivo.

The pharmaceutical composition in the present invention can be used as a pharmaceutical composition that enhances chondrogenesis or increases cartilage matrix production. Examples of target cartilage include hypertrophic cartilage (growth cartilage) and permanent cartilage (articular cartilage). The pharmaceutical composition in the present invention is an inducer of chondrocyte proliferation and differentiation or a chondrogenesis enhancer. Also, the pharmaceutical composition in the present invention can be used for prevention or treatment of a chondropathies. Examples of chondropathies include cartilage defects caused by external injuries or surgical treatment, osteochondritis dissecans, articular rheumatism, osteoarthritis, congenital chondropathies (achondrogenesis), and cartilage injury (e.g., medial meniscus injury). Examples of target test animals include mammalian animals, such as humans, bovines, horses, pigs, sheep, goats, cats, dogs, rabbits, rats, and mice.

A dose of the pharmaceutical composition in the present invention varies depending on symptoms, age, body weight, and other conditions. In general, a dose is approximately 0.01 mg to 10,000 mg per adult per day in the case of oral administration, and such amount of the pharmaceutical composition can be administered once or several separate times. In the case of parenteral administration, the pharmaceutical composition can be administered locally to the location of damaged or lost cartilage or to the cartilage of a patient having one of the above chondropathies.

The pharmaceutical composition in present invention can comprise a carrier, a diluent, and an excipient that are generally used in the field of formulations. For example, lactose, magnesium stearate, and the like can be used as carriers or excipients for tablets. Examples of an injectable aqueous liquid that can be used include a physiological salt solution and an isotonic solution comprising glucose and other adjuvants. Such injectable aqueous liquid can be used in combination with an appropriate solubilizing agent such as alcohol, polyalcohol (e.g., propylene glycol), or a non-ionic surface active agent. Examples of an oily liquid that can be used include sesame oil and soybean oil. Such oily liquid can be used in combination with a solubilizing agent such as benzyl benzoate or benzyl alcohol.

The present invention further concerns a method for screening of a compound that acts on the prechondrocytes and/or mesenchymal stem cells and accelerates differentiation, proliferation, and maturation of such cells, enhances chondrocyte differentiation, induces chondrocyte proliferation, or increases cartilage matrix production; for example, a compound that acts on RANKL, acts on the prechondrocytes and/or mesenchymal stem cells, and accelerates differentiation, proliferation, and maturation of such cells, enhances chondrocyte differentiation, induces chondrocyte proliferation, or increases cartilage matrix production.

In the screening method of the present invention, a candidate compound is added to the prechondrocytes and/or mesenchymal stem cells, and determined whether or not the candidate compound accelerates differentiation of the above cells. For example, a candidate compound can be added to cells having properties similar to the prechondrocytes and/or mesenchymal stem cells, and determined whether or not the candidate compound acts on RANKL and accelerates differentiation and proliferation of the above cells. Differentiation can be measured the elevated expression level of α1-chain of type II collagen in the cells or detected by alcian blue staining. When a candidate compound accelerates proliferation of these cells, it can be determined that the candidate compound is a compound that acts on the prechondrocytes and/or mesenchymal stem cells and accelerates differentiation, proliferation, and maturation of such cells, accelerates chondrocyte differentiation, induces chondrocyte proliferation, or increases cartilage matrix production; that is, a compound that acts on RANKL, acts on the prechondrocytes and/or mesenchymal stem cells, and accelerates differentiation, proliferation, and maturation of such cells, enhances chonrrocyte differentiation, induces chondrocyte proliferation, or increases cartilage matrix production.

Also, a candidate compound can be administered to a mouse, for example, topically to a C57BL/6CrjCrlj mouse, determined whether or not chondrocyte proliferation is observed, and the result may be used to determine that the candidate compound acts on the prechondrocytes and/or mesenchymal stem cells and accelerates differentiation, proliferation, and maturation of such cells, enhances chondrocyte differentiation, induces chondrocyte proliferation, or increases cartilage matrix production; that is, a compound that acts on RANKL, acts on the prechondrocytes and/or mesenchymal stem cells, and accelerates differentiation, proliferation, and maturation of such cells, enhances chondrocyte differentiation, induces chondrocyte proliferation, or increases cartilage matrix production.

The present invention is described in greater detail with reference to the following examples, although the technical scope of the present invention is not limited thereto.

Example 1

Induction of Human Mesenchymal Stem Cell Differentiation Reagent

A synthetic peptide was used for the experiment. Synthetic peptide D is a peptide comprising the amino acid sequence as shown in SEQ ID NO: 7, it is composed of 9 amino acid residues, and it is a cyclic peptide comprising two cysteine residues bound by a disulfide bond. It is reported that synthetic peptide D binds to RANKL (Aoki et al., J. Clin. Invest., 116: 1525, 2006).

Cultured Cell

Human mesenchymal stem cells were purchased from Lonza. A maintenance medium was purchased from Lonza.

Induction of Human Mesenchymal Stem Cell Differentiation

Human mesenchymal stem cells were seeded at $5 \times 10^4$ cells/well in 48-well plate (IWAKI). The culture supernatant was removed 24 hours later, the medium was replaced with a chondrocyte differentiation induction medium (Lonza), and the medium was replaced with fresh medium every 3 or 4 days. Simultaneously, peptide D was added at 100 μM (the group to which peptide D was administered). Further, a group cultured with 100 μM peptide D and 1 ng/ml BMP-4 (R&D) was examined. BMP-4 was added at 1 ng/ml as a positive control group. After 14 days, these cells were fixed in 10% neutral buffered formalin. After fixation, the cells were stained with an alcian blue solution for 4 hours, and the culture plate was photographed. Moreover the pigment was eluted using a 6M guanidinium hydrochloride solution from the culture plate. The eluate (100 μl) was moved to a new 96-well plate, and measured the absorbance at 620 nm by microplate reader (BMG Labtech).

Alcian blue solution (pH 2.5)
Alcian blue 8GX: 1 g
Acetic acid: 3 ml
Distilled water: 97 ml In FIG. 1A, the alcian blue positive cells were increased with the addition of peptide D compared with control. Further, the absorbance of the eluate at 620 nm in the peptide D group indicated significant increase than that of control group (FIG. 1B). This result indicated that human mesenchymal stem cells were differentiated into chondrocytes with the addition of peptide D. However, synergistic effects between peptide D and BMP-4 were not observed.

Example 2

Induction of Prechondrocyte Differentiation by Peptide D Cultured Cells

The culture cells (ATDC5) derived from a mouse chondrogenic EC (embryonal carcinoma) cell was provided by Professor Hiraki and Associate Professor Shukunami in the Institute for Frontier Medical Sciences, Kyoto University. DMEM/F-12 medium (Cellgro) containing 5% FBS (Nichirei) was used as a maintenance medium.

Induction of Differentiation of ATDC5 Cells

ATDC5 cells were seeded at $2 \times 10^4$ cells/well in a 48-well plate (IWAKI). The culture supernatant was removed 24 hours later, and DMEM/F-12 medium containing 10 ng/ml insulin (Roche) and transferrin (Roche) were added. The medium was replaced with fresh medium every 3 or 4 days.

Simultaneously, peptide D was added at 25 μM and 100 μM. One ng/ml and 5 ng/ml BMP-4 (R&D) were added as positive control. In order to examine the synergistic effects of peptide D and BMP-4, further, 25 μM peptide D and 1 ng/ml BMP-4 were added. After 14 days, these cells were fixed in 10% neutral buffered formalin. After fixation, the cells were stained with an alcian blue solution for 4 hours, and the culture plate was photographed.

Figure 2:
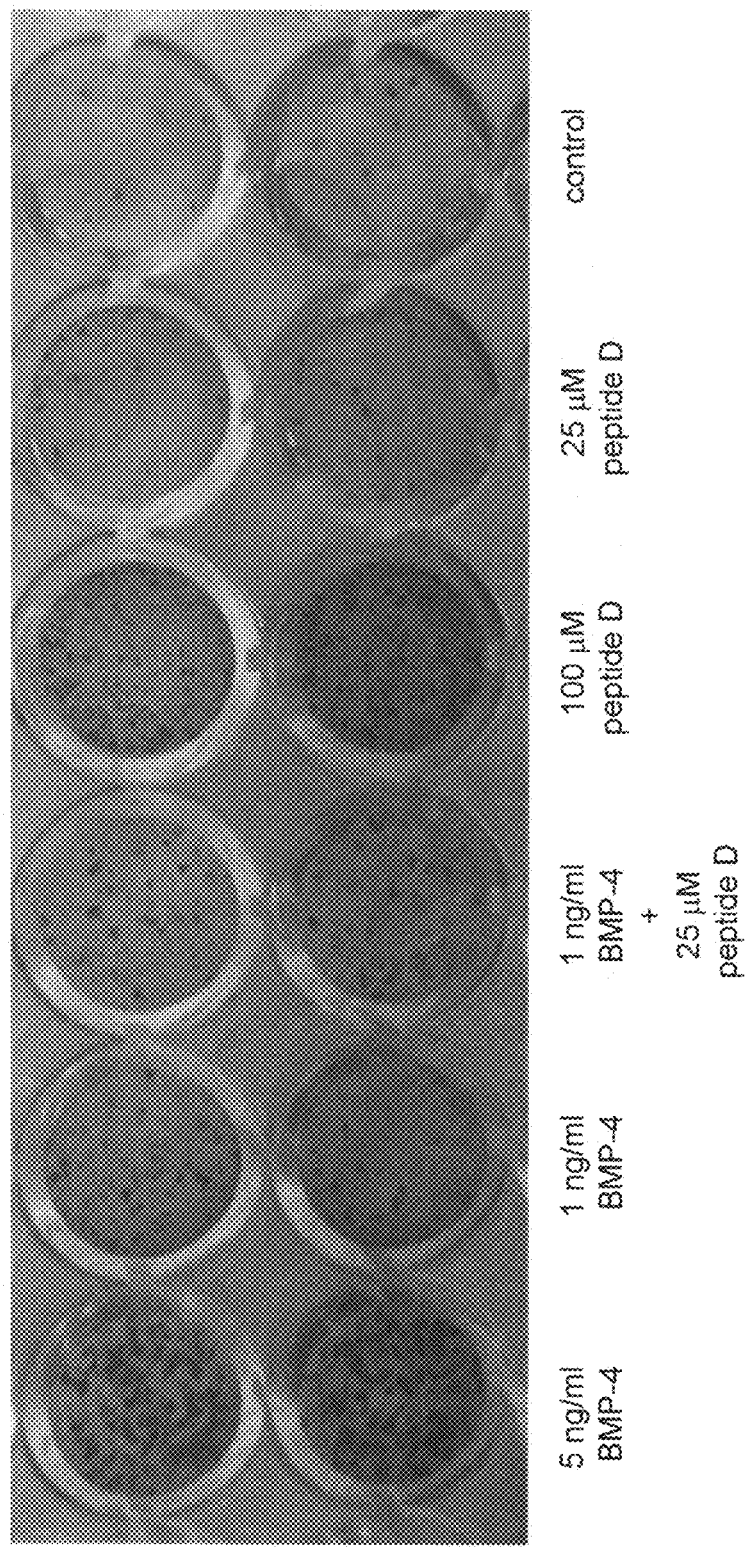
FIG. 2 is a photograph showing induction of chondrocyte differentiation of ATDC5 cells treated with peptide D with alcian blue staining.

Formation of alcian blue positive nodules was observed with the addition of peptide D in ATDC5 cells, and the number thereof increased in a dose dependent manner (FIG. 2). This result indicates that ATDC5 cells were differentiated into chondrocytes with the addition of peptide D.

The synergistic effects between peptide D and BMP-4 were not observed in ATDC5 cells.

Example 3

Expression of Factors in Mouse ATDC5 Cells with the Addition of Peptide D RT-PCR Analysis Mouse prechondrocytes, ATDC5 cells ($5 \times 10^4$ cells) were seeded in a 6-cm dish (IWAKI) and cultured in the presence of a cartilage differentiation induction medium containing 10 ng/ml insulin and transferrin for 7 days and for 14 days. The peptide D group was added at 200 μM peptide D, and 5 ng/ml of BMP-4 was added to the positive control group. The cells were washed with PBS after culture, the cells were dissolved in 1 ml TRIZOL (Qiagen), and the solution was obtained. After 5 min at room temperature, 0.2 ml of chloroform (Wako) was added, followed by vigorous inversion mixing and centrifugation at 4° C. and 12,000×g for 15 minutes. The supernatant was collected in a new tube, and was added to 0.5 ml of isopropanol (Nacalai), followed by inversion mixing. The resultant was left at room temperature for 10 minutes and centrifuged at 4° C. and 12,000×g for 10 minutes. The supernatant was discarded, and the resultant was added to 70% ethanol. After dry-up, RNA was dissolved in 87.5 μl of DEPC water, 10 μl of RDD buffer and 2.5 μl of DNase, and the mixture was allowed to stand at room temperature for 10 minutes. The RNA sample was cleaned by the RNeasy MinElute Cleanup Kit (Qiagen), and the concentration of the obtained RNA was measured using NanoDrop. The obtained RNA (250 ng) was electrophoresed on 1% agarose gel, checked degradation of RNA, and undegraded RNA samples (250 ng each) were used in RT-PCR. RT-PCR was carried out using the ThermoScript RT-PCR System (Invitrogen) and random primers.

After cDNA was synthesized, PCR was carried out using primers specific for the α1 chains of mouse type II collagen (mCol 2α1), mouse type X collagen (mCol X), and mouse aggrecan (mAggrecan). PCR was carried out using mouse GAPDH-specific primers for standardization. The sequences of PCR primers used are shown below. PCR was carried out under the conditions described below with the use of Ex Taq™ Hot Start Version (Takara Bio Inc.).

The α1 chain of mouse type II collagen (mCol 2α1) was subjected to initial thermal denaturation at 95° C. for 3 minutes, followed by 37 cycles of 95° C. for 10 seconds, 48° C. for 15 seconds, and 68° C. for 30 seconds, and an elongation reaction at 68° C. for 10 minutes.

Mouse type X collagen (mCol X) was subjected to initial thermal denaturation at 95° C. for 3 minutes, followed by 34 cycles of 95° C. for 10 seconds, 54° C. for 15 seconds, and 68° C. for 30 seconds, and an elongation reaction at 68° C. for 10 minutes.

Mouse aggrecan (mAggrecan) was subjected to initial thermal denaturation at 95° C. for 3 minutes, followed by 40 cycles of 95° C. for 10 seconds, 54° C. for 15 seconds, and 68° C. for 30 seconds, and an elongation reaction at 68° C. for 10 minutes.

Mouse GAPDH was subjected to initial thermal denaturation at 95° C. for 3 minutes, followed by 23 cycles of 94° C. for 10 seconds, 58° C. for 15 seconds, and 68° C. for 30 seconds, and an elongation reaction at 68° C. for 10 minutes. mCol X, was subjected to 37 cycles on day 14 and the resulting data was obtained.

PCR Primer Sequences

```
                                         (SEQ ID NO: 8)
mCol 2α1-F: 5'-GATGACATTATCTGTGAAG-3'

(SEQ ID NO: 9)
mCol 2α1-R: 5'-ATCTCTGATATCTCCAGG-3'

(SEQ ID NO: 10)
mCol X-F: 5'-CTTTGTGTGCCTTTCAATCG-3'

(SEQ ID NO: 11)
mCol X-R: 5'-GTGAGGTACAGCCTACCAGTT-3'

(SEQ ID NO: 12)
mAggrecan-F: 5'-AACTTCTTTGCCACCGGAGA-3'

(SEQ ID NO: 13)
mAggrecan-R: 5'-GGTGCCCTTTTTACACGTGAA-3'

(SEQ ID NO: 14)
mGAPDH-F: 5'-CACCATGGAGAAGGCCGGGG-3'

(SEQ ID NO: 15)
mGAPDH-R: 5'-GACGGACACATTGGGGGTAG-3'
```

Figure 3A:
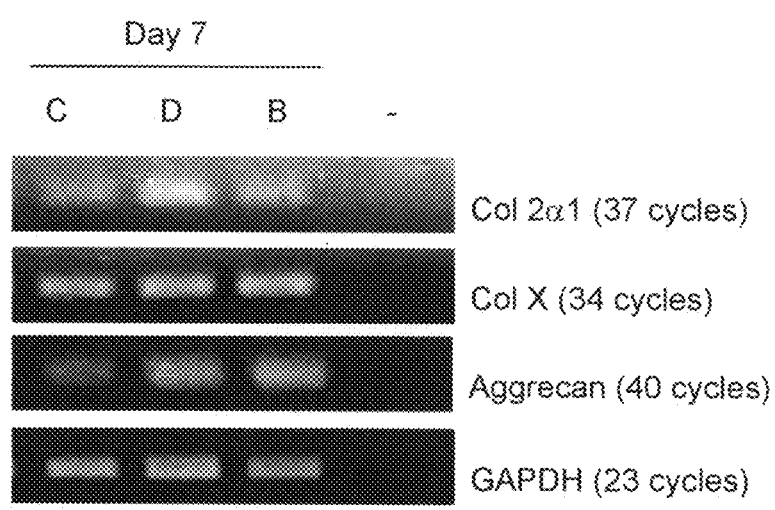
FIG. 3A is a photograph showing expression of factors by RT-PCR in mouse ATDC5 cells on day 7 after the addition of peptide D.
Figure 3B:
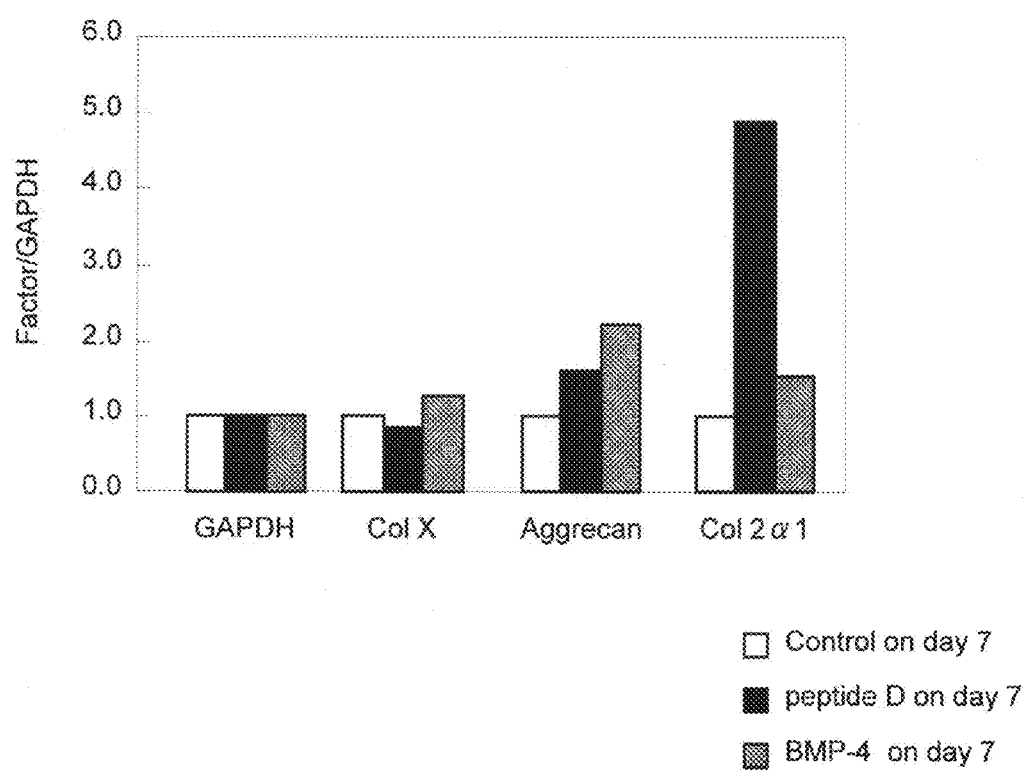
FIG. 3B is a chart showing GAPDH-standardized expression of chondrocytic factors by RT-PCR in mouse ATDC5 cells on day 7 after the addition of peptide D.
Figure 4A:
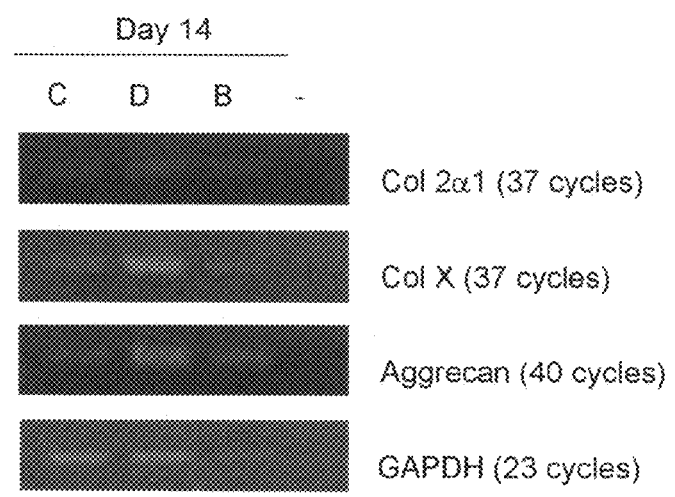
FIG. 4A is a photograph showing expression of chondrocytic factors by RT-PCR in mouse ATDC5 cells on day 14 after the addition of peptide D.

The sample obtained after PCR was electrophoresed on 2% agarose gel, and a specific band was detected by UV with the use of ethidium bromide staining (FIG. 3A and FIG. 4A). The obtained image was analyzed using the CSAnalyzer (ATTO). The results were standardized with the GAPDH expression level and are shown in FIG. 3B and in FIG. 4B.

Figure 4B:
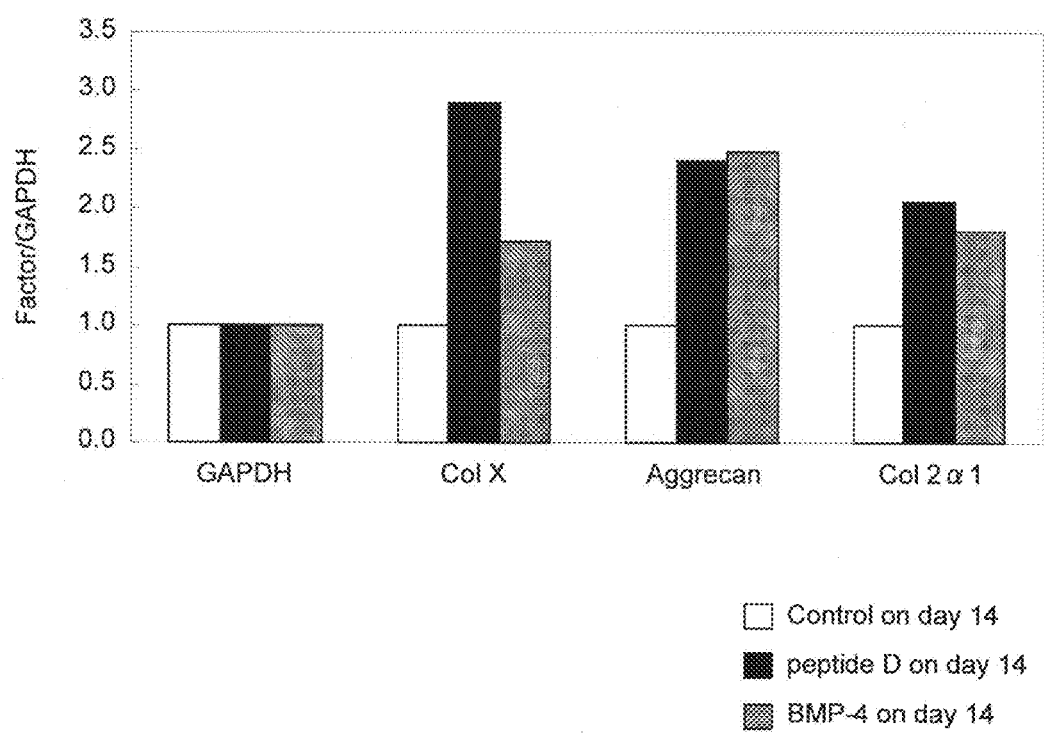
FIG. 4B is a chart showing GAPDH-standardized expression of chondrocytic factors by RT-PCR in mouse ATDC5 cells on day 14 after the addition of peptide D.

As a result, the aggrecan expression level was increased on day 7 in ATDC5 cells treated with peptide D, and the expression level of the α chain of type II collagen was significantly increased compared with the control (FIG. 3A and FIG. 3B). Further, the expression level of type X collagen had particularly increased on day 14 in ATDC5 cells treated with peptide D (FIG. 4A and FIG. 4B). The results indicate that the expression levels of the genes specific for chondrocyte differentiation are elevated with the addition of peptide D in ATDC5 cells.

Example 4

GeneChip Analysis Using ATDC5 Cells

Reagent/Cultured Cells

The peptide described in Example 1 was used. The ATDC5 cells described in Example 2 were used as cultured cells. The ATDC5 cells were seeded in a 6-cm dish (IWAKI) at $1 \times 10^5$ cells/well. The culture supernatant was removed 72 hours later, and DMEM/F-12 medium containing 10 ng/ml insulin (Roche) and 10 ng/ml transferrin (Roche) was added. The medium was replaced with fresh medium every 3 or 4 days.

Simultaneously, peptide D was added at 100 µM. The medium was removed 4 days and 7 days after the induction of differentiation. The cells were washed with PBS, and RNA of these cells was obtained using the Absolutely RNA Miniprep Kit (Stratagene) 7 days after the induction of differentiation. The extracted RNA was subjected to GeneChip analysis (Affimetrix, Kurabo). The expression levels of factors that were significantly increased or decreased with the addition of peptide D were calculated by the ratio of signal value treated with peptide D divided by the signal value of the control group.

Figure 5:
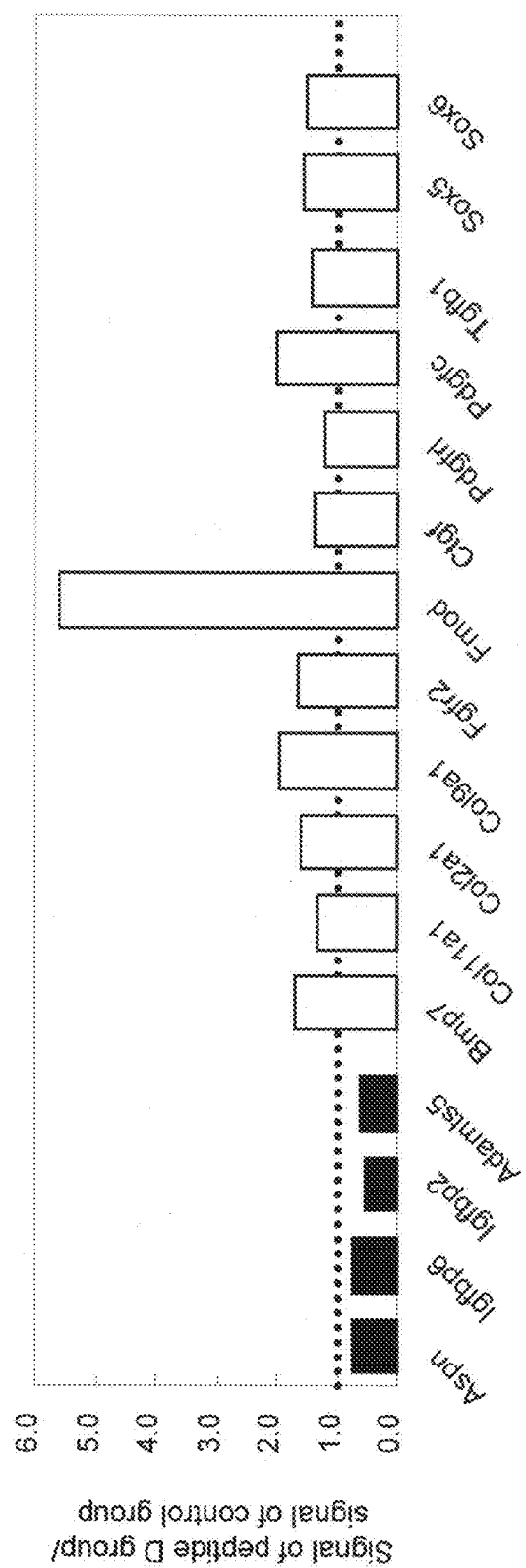
FIG. 5 shows an increase/decrease in expression of chondrocytic factors by GeneChip analysis in mouse ATDC5 cells treated with peptide D.

The results are shown in FIG. 5. As shown in FIG. 5, the expression levels of the α chains of type II, IX, and XI collagens as cartilage matrices were increased, and the expression levels of factors such as CTGF, PDGF, TGFβ1, and fibromodulin, which were reported to be involved in induction of differentiation, and receptors thereof (e.g., PDGFR1 and FGFR2) were also increased. In addition, the expression level of BMP-7 inducing chondrocyte differentiation was increased.

Further, expression of asporin, IGFbp2, IGFbp6, and ADAMTS5 that have been reported to be involved in the progression of osteoarthritis was inhibited with the addition of peptide D. Thus, it was confirmed that the ATDC5 cells were differentiated into chondrocytes with the addition of peptide D.

Example 5

Cell Proliferating Activity of Antibody Using ATDC5 Cells Reagent/Cultured Cells The ATDC5 cells described in Example 2 were used as cultured cells. The anti-RANKL monoclonal antibodies mmB (clone 12A668, Santa Cruz), 1-12H (clone 1-12H, Oriental Yeast Co., Ltd.), mh2 (clone 70513, R&D), sc55 (clone 4i167, Santa Cruz), and sc72 (clone 500-M46, Santa Cruz) and the monoclonal antibody FL317 (Santa Cruz) were used. As a positive control sample, $2 \times 10^{-4}$ M FGF2 (Fiblast Spray, Kaken Pharmaceutical Co., Ltd.) was used.

The ATDC5 cells ($4 \times 10^3$ cells) were seeded in a 96-well plate, and the medium was replaced with a serum-free medium after the cells had adhered. The antibodies were added at 5 µg/ml 16 hours later. Ten µl of WST-1 (Roche) was added per 100 µl of the solution after 72 hours culture, and the absorbance at 450 nm (reference wavelength: 595 nm) was measured using a microplate reader with the elapse of time for 1 to 4 hours at 37° C.

Figure 6:
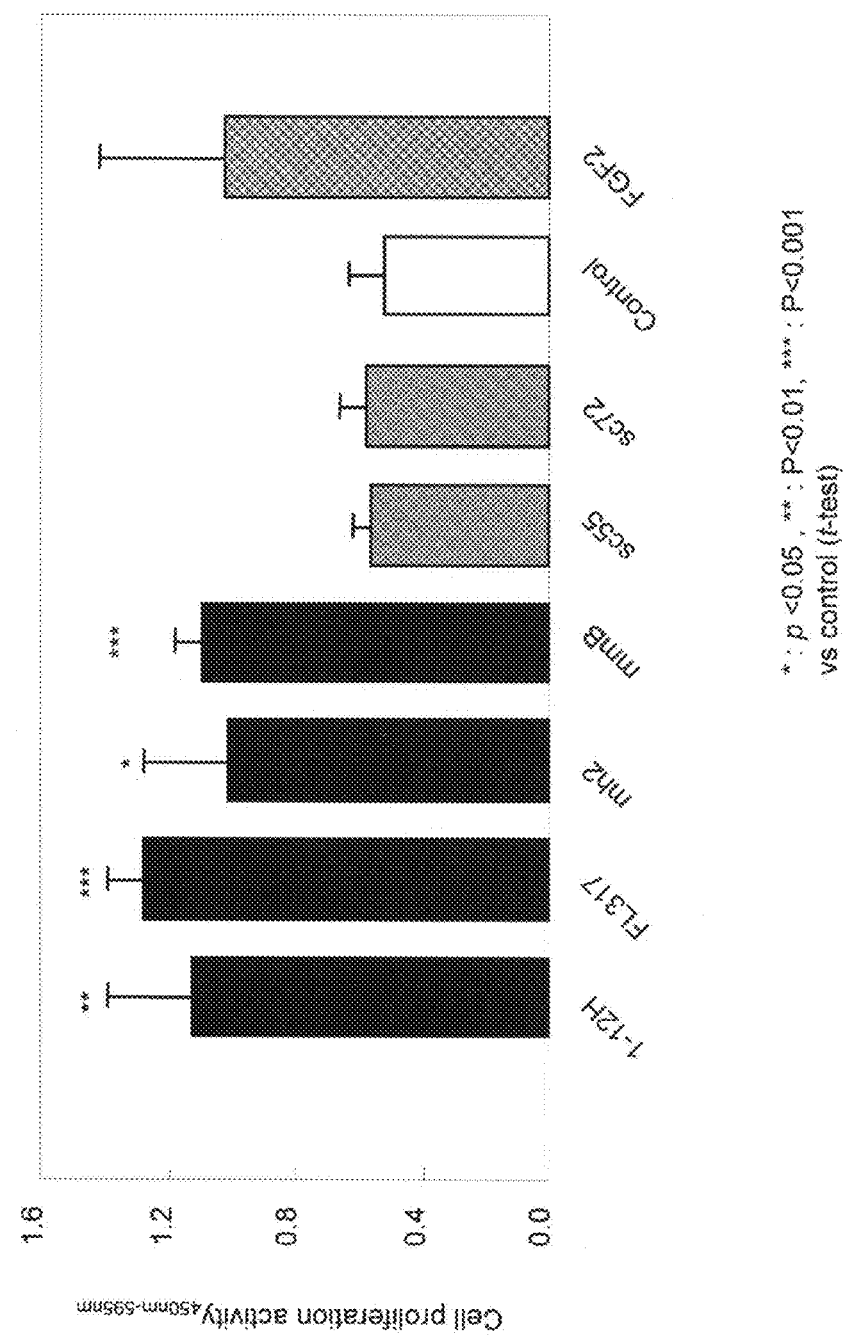
FIG. 6 shows an increase in proliferative response of mouse ATDC5 cells treated with the anti-RANKL antibodies.

As a result, the ATDC5 proliferation activity was significantly increased with the addition of the anti-RANKL polyclonal antibody FL317 and the anti-RANKL monoclonal antibodies 1-12H, mmB, and mh2 (FIG. 6).

Example 6

Induction of Chondrocyte Differentiation by Antibody

Reagent/Cultured Cells

The ATDC5 cells described in Example 2 were used as cultured cells. The mmB antibody described in Example 5 and the anti-RANKL monoclonal antibody mmC (clone 12A380, ALEXIS) were used.

The ATDC5 cells were seeded in a 48-well plate (IWAKI) at $2\times10^4$ cells/well. The culture supernatant was removed 72 hours later, the medium was replaced with the differentiation induction medium described in Example 5, and the medium was replaced with fresh medium every 3 or 4 days. Simultaneously, the mmB antibody and the mmC antibody were added at 0.5 µg/ml, on day 14 these cells were fixed in 10% neutral buffered formalin. After fixation, alcian blue staining was carried out in the manner described in Example 2, and nodule formation was observed.

Figure 7:
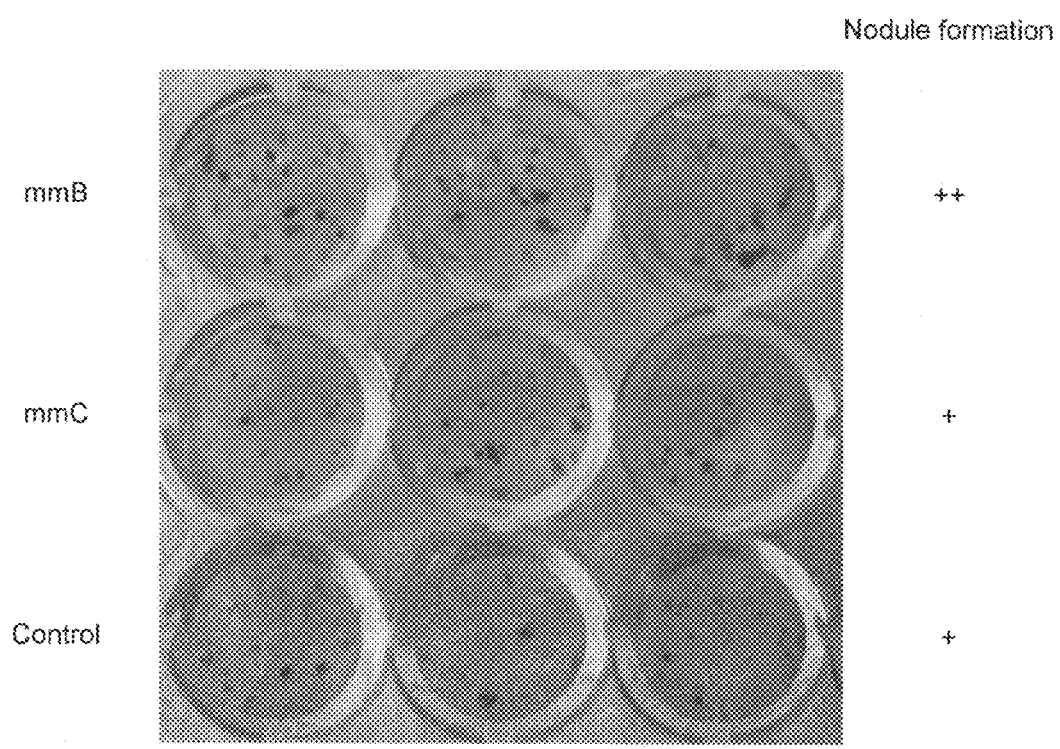
FIG. 7 is a photograph showing differentiation of mouse ATDC5 cells into chondrocytes treated with the anti-RANKL monoclonal antibodies.

The results are shown in FIG. 7. It was apparent that the number of cells stained positive for alcian blue had become larger with the addition of the mmB antibody and nodule formation had increased. This demonstrates that differentiation of ATDC5 cells into chondrocytes proceeded with the addition of the mmB antibody.

Example 7

Three-Dimensional Culture Using Human Mesenchymal Stem Cells

Reagent/Cultured Cells

Figure 8:
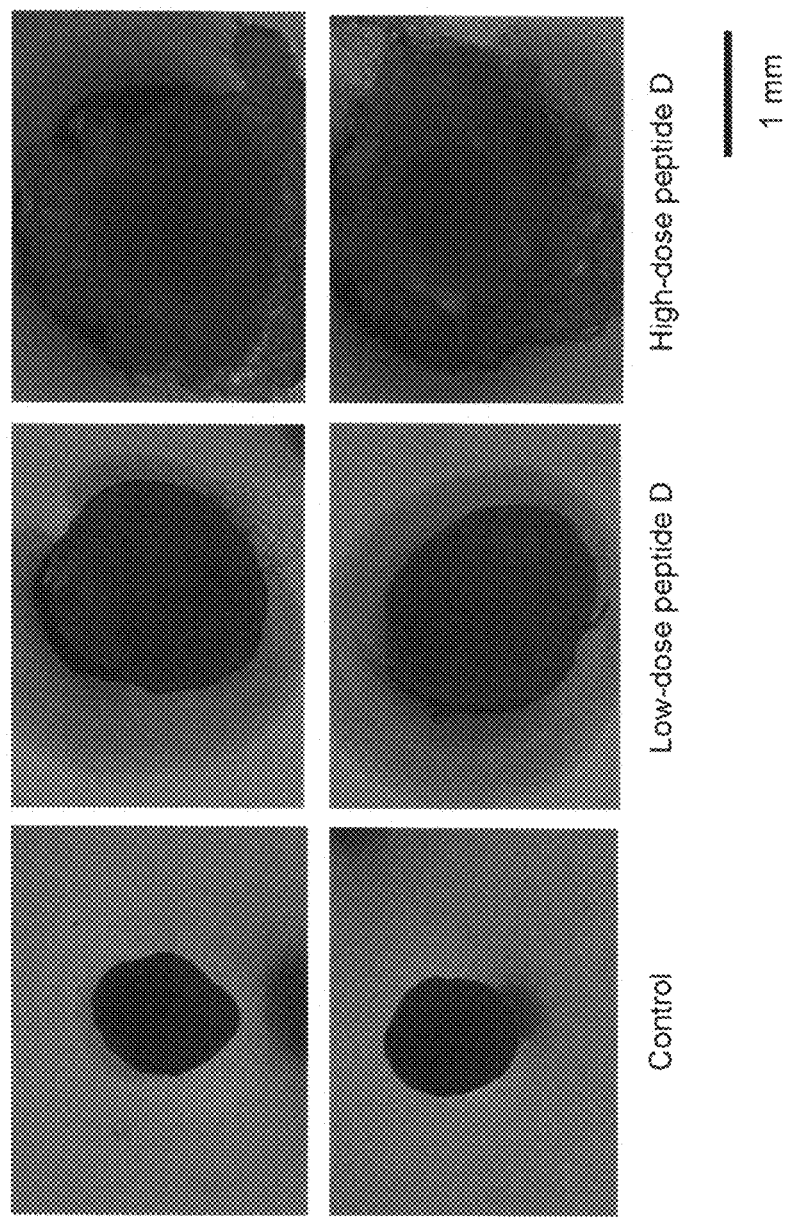
FIG. 8 is a photograph of a 3-dimensional culture pellet in human mesenchymal stem cells treated with peptide D.
Figure 9:
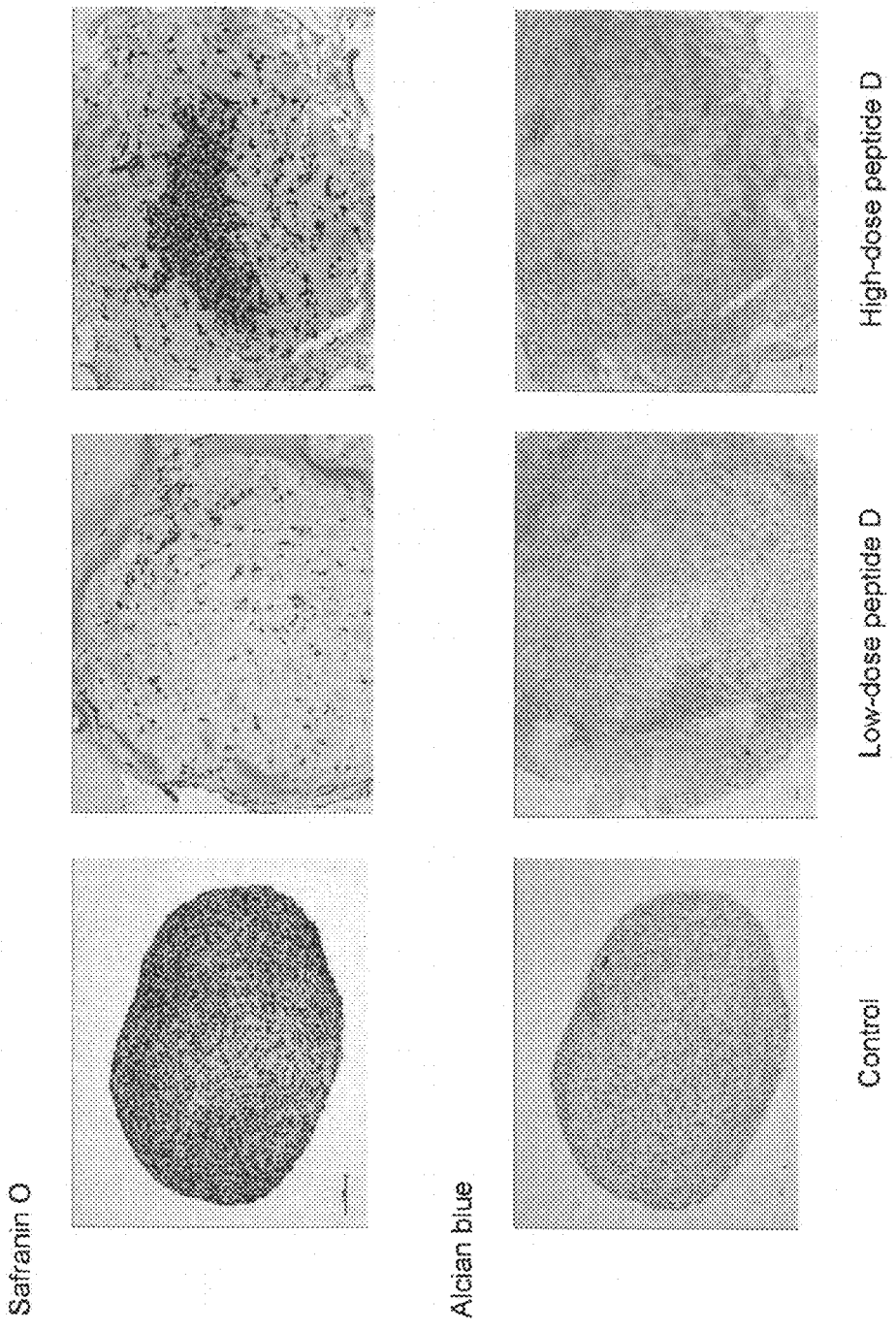
FIG. 9 is a photograph showing alcian-blue-stained slide samples and safranin-O-stained slide samples of 3-dimensional culture pellet in human mesenchymal stem cells treated with peptide D.

The peptide described in Example 1 was used. Human mesenchymal stem cells were purchased from Lonza. A maintenance medium was purchased from Lonza. Three-dimensional culture of human mesenchymal stem cells Chondrocytes are three-dimensionally cultured induce dedifferentiation. Three dimensional culture system relatively reflected the natural conditions. Human mesenchymal stem cells were seeded at $2.5\times10^5$ cells in 15-ml tubes (TPP) and the cells were collected by centrifuged at 1,000 rpm and room temperature for 4 minutes. The supernatant was removed and the medium was replaced with 0.5 ml chondrocyte differentiation induction medium (Lonza) with 10 ng/ml TGF-β3 (R&D). The medium was replaced with fresh medium every 3 or 4 days. Simultaneously, peptide D was added at 50 µM and at 150 µM (i.e., a low-dose peptide D group and a high-dose peptide D group). After 14 days, the cells were fixed in 4% PFA (Wako), photographed under a microscope (FIG. 8). A pellet was embedded in paraffin, and the sample slide was prepared, followed by alcian blue staining and safranin 0 staining (FIG. 9). The results were shown in FIG. 8 and in FIG. 9. These results indicated that peptide D increased the pellet size in a dose dependent manner. The enlarged 3-dimensional pellets treated with peptide D were positive stained by alcian blue or safranin O. This indicated that the cartilage matrix has been produced. Since the pellet size increased in three-dimensional culture, it was suggested that peptide D has the capacity for cartilage formation in nature and the capacity for increasing cartilage matrix production.

Figure 10:
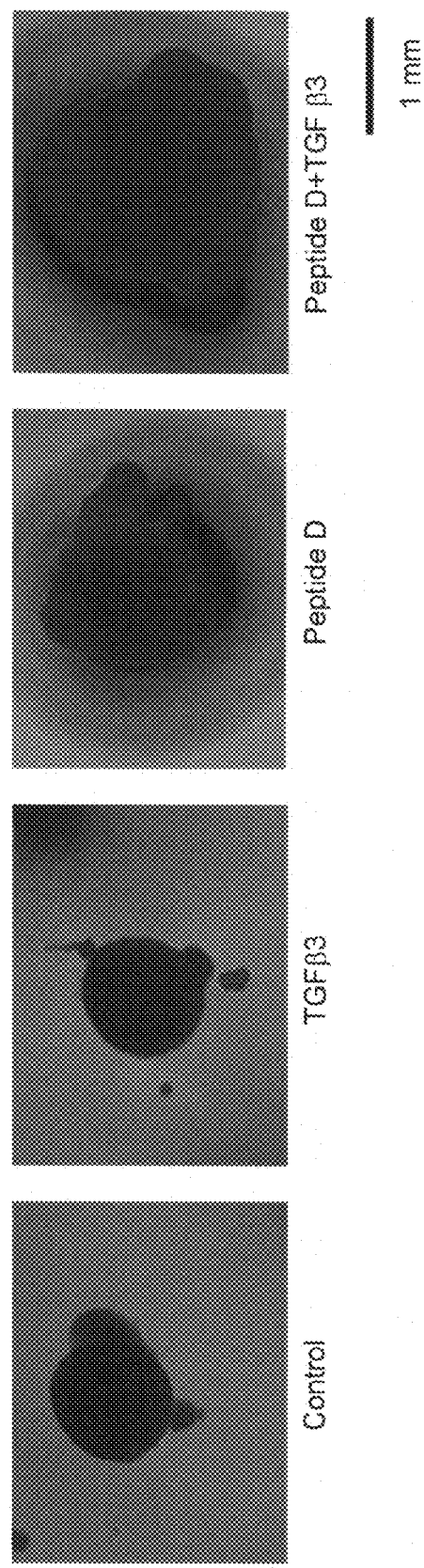
FIG. 10 is a photograph showing the synergistic effects of peptide D and TGF-β3 on forming a 3-dimensional culture pellet of human mesenchymal stem cells.
Figure 11:
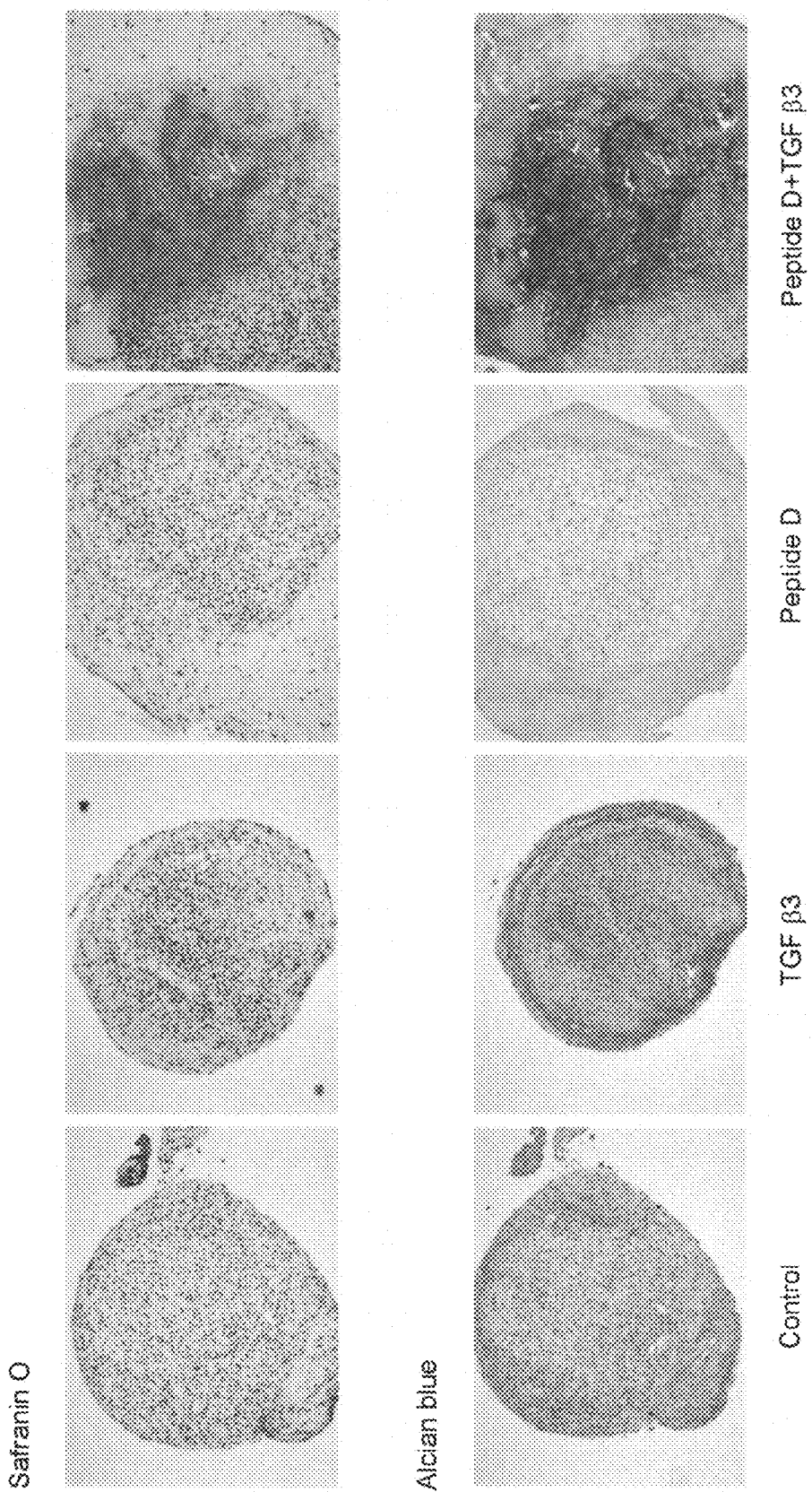
FIG. 11 is a photograph showing alcian-blue-stained slide samples and safranin-O-stained slide samples of 3-dimensional culture pellet in human mesenchymal stem cells exhibiting the synergistic effects of peptide D and TGF-β3.

Subsequently, the synergistic effects of peptide D and TGF-β3 on cartilage formation were examined. $2.5\times10^5$ human mesenchymal stem cells were cultured in the presence of 40 µM peptide D and 10 ng/ml TGF-β3 with cartilage differentiation induction medium for 21 days. After the pellets were fixed in 4% PFA, the pellet was photographed under a microscope (FIG. 10). After the pellet had been embedded in paraffin, the sample slide was prepared and stained with alcian blue and safranin 0 (FIG. 11). The results are shown in FIGS. 10 and 11. The pellet size treated with TGF-β3 alone did not change compared with the control group. The pellet size treated with peptide D and TGF-β3 were increased markedly. Further, the cells treated with peptide D and TGF-β3 were strongly positive for alcian blue or safranin 0 staining. These results demonstrated the synergistic effects of the peptide D and TGF-β3 on chondrocyte differentiation or cartilage matrix production (FIG. 11).

Figure 12:
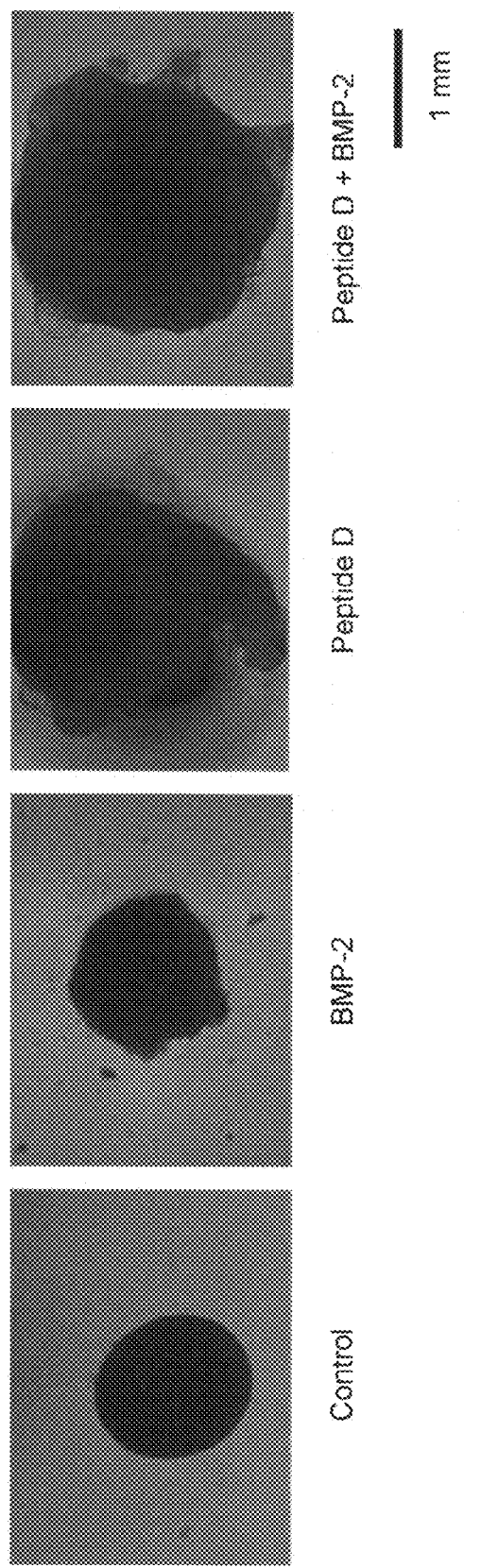
FIG. 12 is a photograph showing the synergistic effects of peptide D and BMP-2 on forming a 3-dimensional culture pellet in human mesenchymal stem cells.
Figure 13:
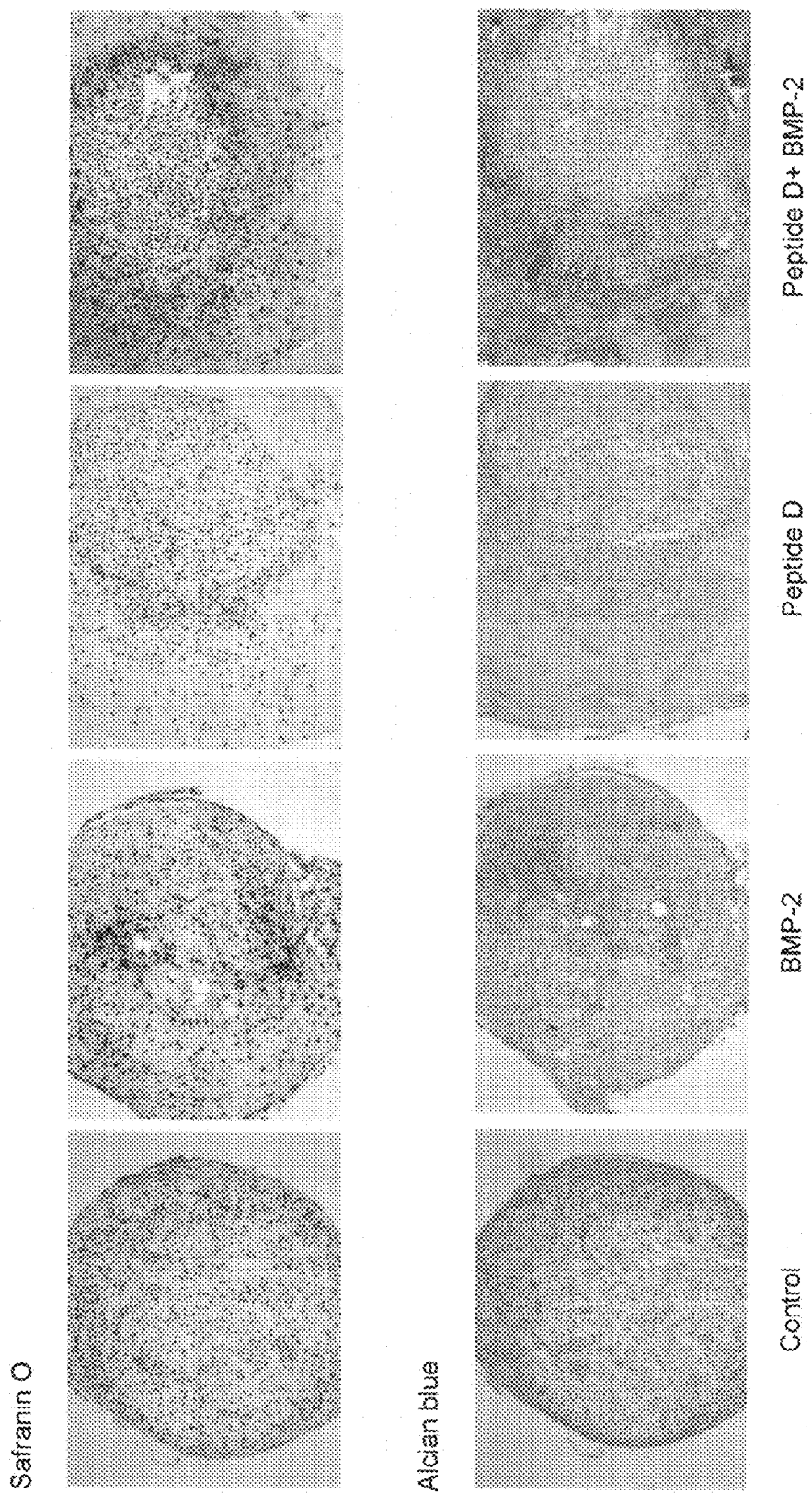
FIG. 13 is a photograph showing alcian-blue-stained slide samples and safranin-O-stained slide samples of three-dimensional culture pellet in human mesenchymal stem cells exhibiting the synergistic effects of peptide D and BMP-2.

Moreover, the synergistic effects of peptide D and BMP-2 were examined. $2.5\times10^5$ human mesenchymal stem cells were cultured in the presence of 40 µM peptide D and 100 ng/ml BMP-2 (R&D) with cartilage differentiation induction medium for 21 days. After the pellets were fixed in 4% PFA, the pellet was photographed under a microscope (FIG. 12). After the pellet had been embedded in paraffin, the sample slide was prepared and stained with alcian blue and safranin O (FIG. 13). The results are shown in FIGS. 12 and 13. The pellet size treated with BMP-2 alone did not change compared with the control group. The pellet size treated with peptide D and BMP-2 did not change compared with that of peptide D (FIG. 12). In spite of no change of the pellet size, the pellet treated with peptide D and BMP-2 was strongly positive for alcian blue or safranin O staining. The synergistic effects of peptide D and BMP-2 was shown on chondrocyte differentiation or cartilage matrix production, but no effect on pellet size was observed.

Example 8

GeneChip Analysis Using Human Mesenchymal Stem Cells

Reagent/cultured cells

The peptide described in Example 1 was used. Human mesenchymal stem cells were purchased from Lonza. A maintenance medium was purchased from Lonza.

Human mesenchymal stem cells were seeded in a 6-well plate (Nunc) at $1\times10^5$ cells/well, the culture supernatant was discarded 96 hours later, and 2 ml of a cartilage differentiation induction medium was added. The control group, the 40 µM peptide D group, the 10 ng/ml TGF-β3 group, and the 40 µM peptide D+10 ng/ml TGFβ3 group were prepared. Each culture medium was replaced 24 hours after the stimulation. The cells were dissolved in 1 ml of TRIZOL (Invitrogen) 96 hours after the stimulation, and RNA was isolated. The isolated RNA was used for GeneChip analysis (Affimetrix, Kurabo). The expression levels of factors that were significantly increased or decreased with the addition of the peptide D, TGF-β3, or peptide D+TGF-β3 were calculated by the ratio of signal values treated with peptide D, TGF-β3, and peptide D+TGF-β3 divided by the signal value of the control group. The results are shown in FIG. 14.

The expression level of the aggrecan as the cartilage matrix was elevated 24 hours after the addition of peptide D, and the elevated expression level was maintained 96 hours after the addition. In contrast, the aggrecan expression level of the TGF-β3 group was equivalent to that of the control group 24 hours after the addition, but the aggrecan expression level had become lower than that of the control group 96 hours after the addition. The aggrecan expression level in the peptide D+TGF-β3 group was lowered because of the influence of lowered expression caused by TGF-β3. Also, the expression levels of Sox9 (SRY (sex determining region Y)-box 9) involved in chondrocyte differentiation were elevated in the three groups (peptide D, TGF-β3, and peptide D+TGF-β3) 24 hours and 96 hours after the addition, compared with the control group. Peptide D elevated IGF2R and versican expression 24 hours later, and elevated IGF-1, LTBP2, and TGFβ1 expression levels 96 hours later.

Figure 14:
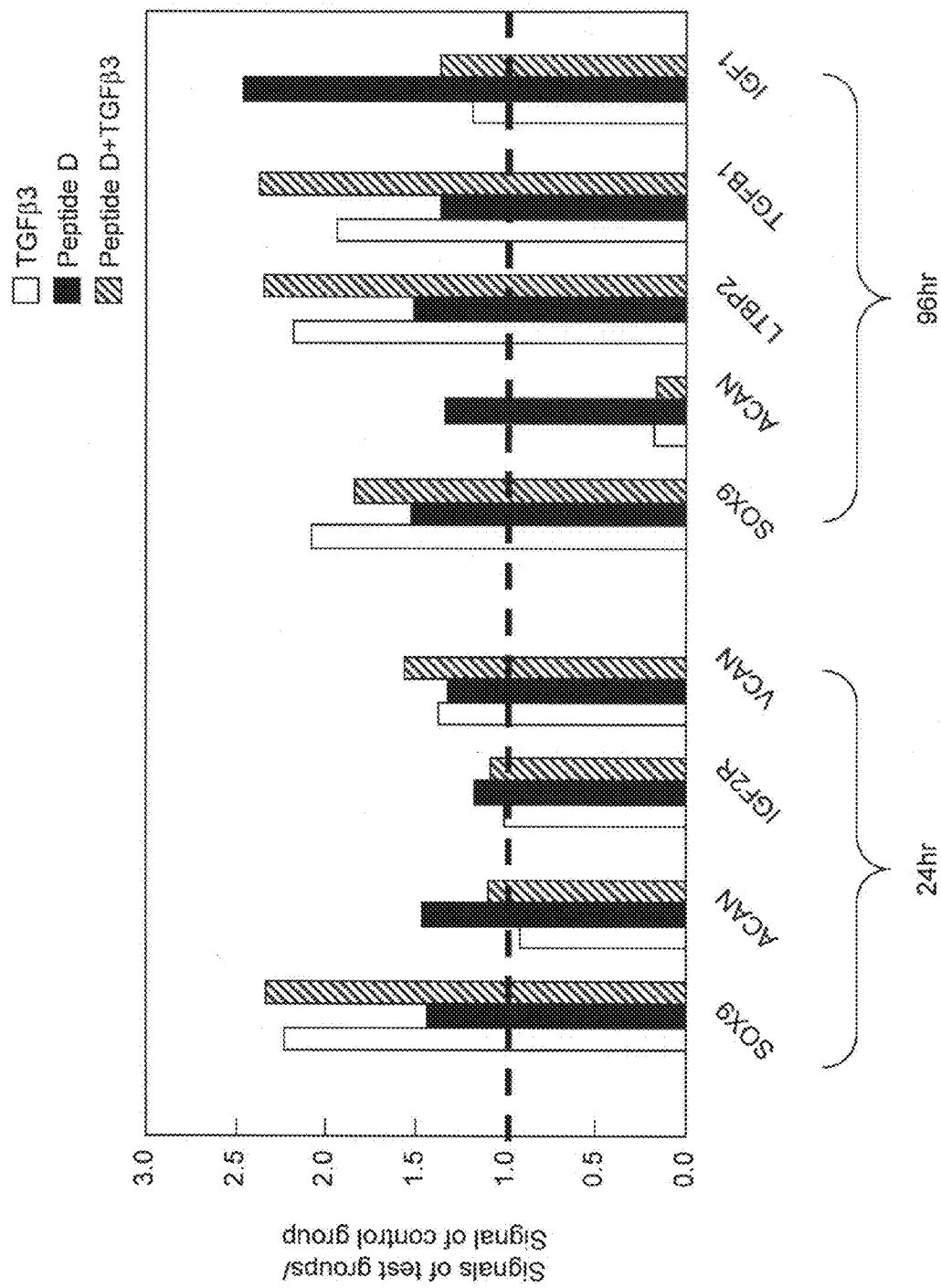
FIG. 14 shows the results of GeneChip analysis using RNA from human mesenchymal stem cells treated with TGF-β3, peptide D, or peptide D plus TGF-β3.

The abbreviations used in FIG. 14 are defined as follows.
ACAN: aggrecan
IGF1: insulin growth factor 1
LTBP2: latent transforming growth factor protein 2
SOX9: SRY (sex determining region Y)-box 9
VCAN: Versican

INDUSTRIAL APPLICABILITY

As described in Examples, prechondrocytes and mesenchymal stem cells are differentiated into chondrocytes, such cells are proliferated, or the cartilage matrices are increased by the molecules that act on membrane RANKL, such as membrane RANK, a RANK analog peptide, an anti-RANKL antibody, soluble RANK, OPG, a mutant thereof, or an analog thereof.

A compound, such as membrane RANK, a RANK analog peptide, an anti-RANKL antibody, soluble RANK, OPG, a mutant thereof, an analog thereof, or a natural or a synthetic low-molecular-weight compound, that acts on the prechondrocytes and/or mesenchymal stem cells and accelerates differentiation, proliferation, and maturation of such cells, enhances chondrocyte differentiation, induces chondrocyte proliferation, or increases cartilage matrix production, for example, a molecule acting on RANKL induces differentiation and proliferation of chondrocytes can be used as a pharmaceutical product for prevention or treatment of a chondropathies. Screening for a compound that acts on prechondrocytes and/or mesenchymal stem cells and accelerates differentiation, proliferation, and maturation of such cells, enhances chondrocyte differentiation, induces chondrocyte proliferation, or increases cartilage matrix production, for example, a molecule acting on RANKL was obtained a compound can be applied to research and development of novel inducers of chondrocyte differentiation and proliferation and agents for increasing cartilage matrix production.

SEQUENCE LISTING FREE TEXT

SEQ ID NO: 7: Synthetic peptide
SEQ ID NOs: 8 to 15: Primers
SEQ ID NOs: 16 and 17: Tag sequences All publications, patents, and patent applications cited herein are incorporated herein by reference in their entirety.

The invention claimed is:

1. A method for (1) inducing human chondrocyte proliferation or (2) inducing differentiation of human mesenchymal stem cells or human prechondrocytes into chondrocytes, comprising: contacting a peptide consisting of the amino acid sequence as shown in SEQ ID NO: 7 or a salt thereof with the human mesenchymal stem cells or the human prechondrocytes of a human patient by administering the peptide consisting of the amino acid sequence as shown in SEQ ID NO: 7 or a salt thereof locally to a cartilage of the human patient.

2. The method according to claim 1, wherein the peptide consisting of the amino acid sequence as shown in SEQ ID NO: 7 is fused with (1) Flag represented by the amino acid sequence DYKDDDDK (SEQ ID NO: 16) or DYLDDDDL (SEQ ID NO: 17), (2) glutathione-S-transferase, or (3) an Fc region of immunoglobulin G, wherein the peptide consisting of the amino acid sequence as shown in SEQ ID NO: 7 fused with (1) Flag represented by the amino acid sequence DYKDDDDK (SEQ ID NO: 16) or DYLDDDDL (SEQ ID NO: 17), (2) glutathione-S-transferase, or (3) an Fc region of immunoglobulin G is administered locally to the cartilage.

3. A method for increasing human cartilage matrix production, comprising: contacting a peptide consisting of the amino acid sequence as shown in SEQ ID NO: 7 or a salt thereof with the human mesenchymal stem cells of a human patient by administering the peptide consisting of the amino acid sequence as shown in SEQ ID NO: 7 or a salt thereof locally to a cartilage of the human patient.

4. The method for increasing human cartilage matrix production according to claim 3, wherein the peptide consisting of the amino acid sequence as shown in SEQ ID NO: 7 is fused with (1) Flag represented by the amino acid sequence DYKDDDDK (SEQ ID NO: 16) or DYLDDDDL (SEQ ID NO: 17), (2) glutathione-S-transferase, or (3) an Fc region of immunoglobulin G, wherein the peptide consisting of the amino acid sequence as shown in SEQ ID NO: 7 (1) is fused with Flag represented by the amino acid sequence DYKDDDDK (SEQ ID NO: 16) or DYLDDDDL (SEQ ID NO: 17), (2) glutathione-S-transferase, or (3) an Fc region of immunoglobulin G, is administered locally to the cartilage.

* * * * *

SEQUENCE LISTING

```
<160> NUMBER OF SEQ ID NOS: 17

<210> SEQ ID NO 1
<211> LENGTH: 2201
<212> TYPE: DNA
<213> ORGANISM: Homo sapiens
<220> FEATURE:
<221> NAME/KEY: CDS
<222> LOCATION: (129)..(1082)

<400> SEQUENCE: 1
ggccaaagcc gggctccaag tcggcgcccc acgtcgaggc tccgccgcag cctccggagt      60
tggccgcaga caagaagggg agggagcggg agagggagga gagctccgaa gcgagagggc     120 cgagcgcc atg cgc cgc gcc agc aga gac tac acc aag tac ctg cgt ggc      170
         Met Arg Arg Ala Ser Arg Asp Tyr Thr Lys Tyr Leu Arg Gly
           1               5                  10 tcg gag gag atg ggc ggc ggc ccc gga gcc ccg cac gag ggc ccc ctg       218
Ser Glu Glu Met Gly Gly Gly Pro Gly Ala Pro His Glu Gly Pro Leu
 15              20                  25                  30 cac gcc ccg ccg ccg cct gcg ccg cac cag ccc ccc gcc gcc tcc cgc       266
His Ala Pro Pro Pro Pro Ala Pro His Gln Pro Pro Ala Ala Ser Arg
                 35                  40                  45 tcc atg ttc gtg gcc ctc ctg ggg ctg ggg ctg ggc cag gtt gtc tgc       314
Ser Met Phe Val Ala Leu Leu Gly Leu Gly Leu Gly Gln Val Val Cys
             50                  55                  60 agc gtc gcc ctg ttc ttc tat ttc aga gcg cag atg gat cct aat aga       362
Ser Val Ala Leu Phe Phe Tyr Phe Arg Ala Gln Met Asp Pro Asn Arg
         65                  70                  75 ata tca gaa gat ggc act cac tgc att tat aga att ttg aga ctc cat       410
Ile Ser Glu Asp Gly Thr His Cys Ile Tyr Arg Ile Leu Arg Leu His
     80                  85                  90 gaa aat gca gat ttt caa gac aca act ctg gag agt caa gat aca aaa       458
Glu Asn Ala Asp Phe Gln Asp Thr Thr Leu Glu Ser Gln Asp Thr Lys
 95                 100                 105                 110 tta ata cct gat tca tgt agg aga att aaa cag gcc ttt caa gga gct       506
Leu Ile Pro Asp Ser Cys Arg Arg Ile Lys Gln Ala Phe Gln Gly Ala
                115                 120                 125
```

| | |
|---|---|
| gtg caa aag gaa tta caa cat atc gtt gga tca cag cac atc aga gca<br>Val Gln Lys Glu Leu Gln His Ile Val Gly Ser Gln His Ile Arg Ala<br>          130                            135                    140 | 554 |
| gag aaa gcg atg gtg gat ggc tca tgg tta gat ctg gcc aag agg agc<br>Glu Lys Ala Met Val Asp Gly Ser Trp Leu Asp Leu Ala Lys Arg Ser<br>        145                            150                    155 | 602 |
| aag ctt gaa gct cag cct ttt gct cat ctc act att aat gcc acc gac<br>Lys Leu Glu Ala Gln Pro Phe Ala His Leu Thr Ile Asn Ala Thr Asp<br>160                        165                        170 | 650 |
| atc cca tct ggt tcc cat aaa gtg agt ctg tcc tct tgg tac cat gat<br>Ile Pro Ser Gly Ser His Lys Val Ser Leu Ser Ser Trp Tyr His Asp<br>175                        180                        185                    190 | 698 |
| cgg ggt tgg gcc aag atc tcc aac atg act ttt agc aat gga aaa cta<br>Arg Gly Trp Ala Lys Ile Ser Asn Met Thr Phe Ser Asn Gly Lys Leu<br>                    195                        200                    205 | 746 |
| ata gtt aat cag gat ggc ttt tat tac ctg tat gcc aac att tgc ttt<br>Ile Val Asn Gln Asp Gly Phe Tyr Tyr Leu Tyr Ala Asn Ile Cys Phe<br>        210                            215                    220 | 794 |
| cga cat cat gaa act tca gga gac cta gct aca gag tat ctt caa cta<br>Arg His His Glu Thr Ser Gly Asp Leu Ala Thr Glu Tyr Leu Gln Leu<br>225                        230                        235 | 842 |
| atg gtg tac gtc act aaa acc agc atc aaa atc cca agt tct cat acc<br>Met Val Tyr Val Thr Lys Thr Ser Ile Lys Ile Pro Ser Ser His Thr<br>240                        245                        250 | 890 |
| ctg atg aaa gga gga agc acc aag tat tgg tca ggg aat tct gaa ttc<br>Leu Met Lys Gly Gly Ser Thr Lys Tyr Trp Ser Gly Asn Ser Glu Phe<br>255                        260                        265                    270 | 938 |
| cat ttt tat tcc ata aac gtt ggt gga ttt ttt aag tta cgg tct gga<br>His Phe Tyr Ser Ile Asn Val Gly Gly Phe Phe Lys Leu Arg Ser Gly<br>                    275                        280                    285 | 986 |
| gag gaa atc agc atc gag gtc tcc aac ccc tcc tta ctg gat ccg gat<br>Glu Glu Ile Ser Ile Glu Val Ser Asn Pro Ser Leu Leu Asp Pro Asp<br>        290                            295                    300 | 1034 |
| cag gat gca aca tac ttt ggg gct ttt aaa gtt cga gat ata gat tga<br>Gln Asp Ala Thr Tyr Phe Gly Ala Phe Lys Val Arg Asp Ile Asp<br>305                        310                        315 | 1082 |
| gccccagttt ttggagtgtt atgtatttcc tggatgtttg gaaacatttt ttaaaacaag | 1142 |
| ccaagaaaga tgtatatagg tgtgtgagac tactaagagg catggcccca acggtacacg | 1202 |
| actcagtatc catgctcttg accttgtaga gaacacgcgt atttacctgc agtgggaga | 1262 |
| tgttagactc atggtgtgtt acacaatggt ttttaaattt tgtaatgaat tcctagaatt | 1322 |
| aaaccagatt ggagcaatta cgggttgacc ttatgagaaa ctgcatgtgg gctatgggag | 1382 |
| gggttggtcc ctggtcatgt gccccttcgc agctgaagtg gagagggtgt catctagcgc | 1442 |
| aattgaagga tcatctgaag gggcaaattc ttttgaattg ttacatcatg ctggaacctg | 1502 |
| caaaaaatac ttttctaat gaggagagaa aatatatgta tttttatata atatctaaag | 1562 |
| ttatatttca gatgtaatgt tttctttgca agtattgta aattatattt gtgctatagt | 1622 |
| atttgattca aaatatttaa aaatgtcttg ctgttgacat atttaatgtt ttaaatgtac | 1682 |
| agacatattt aactggtgca ctttgtaaat tccctgggga aaacttgcag ctaaggaggg | 1742 |
| gaaaaaatg ttgtttccta atatcaaatg cagtatattt cttcgttctt tttaagttaa | 1802 |
| tagattttt cagacttgtc aagcctgtgc aaaaaaatta aaatggatgc cttgaataat | 1862 |
| aagcaggatg ttggccacca ggtgcctttc aaatttagaa actaattgac tttagaaagc | 1922 |
| tgacattgcc aaaaaggata cataatgggc cactgaaatt tgtcaagagt agttatataa | 1982 |
| ttgttgaaca ggtgtttttc cacaagtgcc gcaaattgta cctttttttt tttttcaaaa | 2042 | tagaaaagtt attagtggtt tatcagcaaa aaagtccaat tttaatttag taaatgttat    2102 tttatactgt acaataaaaa cattgccttt gaatgttaat ttttttggtac aaaaataaat   2162 ttatatgaaa aaaaaaaaaa aaaaaaaaaa aaaaaaaaa                          2201

<210> SEQ ID NO 2
<211> LENGTH: 317
<212> TYPE: PRT
<213> ORGANISM: Homo sapiens

<400> SEQUENCE: 2

```
Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315
```

<210> SEQ ID NO 3
<211> LENGTH: 3133
<212> TYPE: DNA

<213> ORGANISM: Homo sapiens
<220> FEATURE:
<221> NAME/KEY: CDS
<222> LOCATION: (39)..(1889)

<400> SEQUENCE: 3

```
ccgctgaggc cgcggcgccc gccagcctgt cccgcgcc atg gcc ccg cgc gcc cgg      56
                                          Met Ala Pro Arg Ala Arg
                                          1               5 cgg cgc cgc ccg ctg ttc gcg ctg ctg ctg ctc tgc gcg ctc ctc gcc     104
Arg Arg Arg Pro Leu Phe Ala Leu Leu Leu Leu Cys Ala Leu Leu Ala
            10                  15                  20 cgg ctg cag gtg gct ttg cag atc gct cct cca tgt acc agt gag aag     152
Arg Leu Gln Val Ala Leu Gln Ile Ala Pro Pro Cys Thr Ser Glu Lys
        25                  30                  35 cat tat gag cat ctg gga cgg tgc tgt aac aaa tgt gaa cca gga aag     200
His Tyr Glu His Leu Gly Arg Cys Cys Asn Lys Cys Glu Pro Gly Lys
    40                  45                  50 tac atg tct tct aaa tgc act act acc tct gac agt gta tgt ctg ccc     248
Tyr Met Ser Ser Lys Cys Thr Thr Thr Ser Asp Ser Val Cys Leu Pro
55                  60                  65                  70 tgt ggc ccg gat gaa tac ttg gat agc tgg aat gaa gaa gat aaa tgc     296
Cys Gly Pro Asp Glu Tyr Leu Asp Ser Trp Asn Glu Glu Asp Lys Cys
                75                  80                  85 ttg ctg cat aaa gtt tgt gat aca ggc aag gcc ctg gtg gcc gtg gtc     344
Leu Leu His Lys Val Cys Asp Thr Gly Lys Ala Leu Val Ala Val Val
            90                  95                  100 gcc ggc aac agc acg acc ccc cgg cgc tgc gcg tgc acg gct ggg tac     392
Ala Gly Asn Ser Thr Thr Pro Arg Arg Cys Ala Cys Thr Ala Gly Tyr
        105                 110                 115 cac tgg agc cag gac tgc gag tgc tgc cgc cgc aac acc gag tgc gcg     440
His Trp Ser Gln Asp Cys Glu Cys Cys Arg Arg Asn Thr Glu Cys Ala
    120                 125                 130 ccg ggc ctg ggc gcc cag cac ccg ttg cag ctc aac aag gac aca gtg     488
Pro Gly Leu Gly Ala Gln His Pro Leu Gln Leu Asn Lys Asp Thr Val
135                 140                 145                 150 tgc aaa cct tgc ctt gca ggc tac ttc tct gat gcc ttt tcc tcc acg     536
Cys Lys Pro Cys Leu Ala Gly Tyr Phe Ser Asp Ala Phe Ser Ser Thr
                155                 160                 165 gac aaa tgc aga ccc tgg acc aac tgt acc ttc ctt gga aag aga gta     584
Asp Lys Cys Arg Pro Trp Thr Asn Cys Thr Phe Leu Gly Lys Arg Val
            170                 175                 180 gaa cat cat ggg aca gag aaa tcc gat gcg gtt tgc agt tct tct ctg     632
Glu His His Gly Thr Glu Lys Ser Asp Ala Val Cys Ser Ser Ser Leu
        185                 190                 195 cca gct aga aaa cca cca aat gaa ccc cat gtt tac ttg ccc ggt tta     680
Pro Ala Arg Lys Pro Pro Asn Glu Pro His Val Tyr Leu Pro Gly Leu
    200                 205                 210 ata att ctg ctt ctc ttc gcg tct gtg gcc ctg gtg gct gcc atc atc     728
Ile Ile Leu Leu Leu Phe Ala Ser Val Ala Leu Val Ala Ala Ile Ile
215                 220                 225                 230 ttt ggc gtt tgc tat agg aaa aaa ggg aaa gca ctc aca gct aat ttg     776
Phe Gly Val Cys Tyr Arg Lys Lys Gly Lys Ala Leu Thr Ala Asn Leu
                235                 240                 245 tgg cac tgg atc aat gag gct tgt ggc cgc cta agt gga gat aag gag     824
Trp His Trp Ile Asn Glu Ala Cys Gly Arg Leu Ser Gly Asp Lys Glu
            250                 255                 260 tcc tca ggt gac agt tgt gtc agt aca cac acg gca aac ttt ggt cag     872
Ser Ser Gly Asp Ser Cys Val Ser Thr His Thr Ala Asn Phe Gly Gln
        265                 270                 275
```

-continued

| | |
|---|---|
| cag gga gca tgt gaa ggt gtc tta ctg ctg act ctg gag gag aag aca<br>Gln Gly Ala Cys Glu Gly Val Leu Leu Leu Thr Leu Glu Glu Lys Thr<br>280                             285                          290 | 920 |
| ttt cca gaa gat atg tgc tac cca gat caa ggt ggt gtc tgt cag ggc<br>Phe Pro Glu Asp Met Cys Tyr Pro Asp Gln Gly Gly Val Cys Gln Gly<br>295                             300                         305                       310 | 968 |
| aca tgt gta gga ggt ggt ccc tac gca caa ggc gaa gat gcc agg atg<br>Thr Cys Val Gly Gly Gly Pro Tyr Ala Gln Gly Glu Asp Ala Arg Met<br>                            315                        320                        325 | 1016 |
| ctc tca ttg gtc agc aag acc gag ata gag gaa gac agc ttc aga cag<br>Leu Ser Leu Val Ser Lys Thr Glu Ile Glu Glu Asp Ser Phe Arg Gln<br>                      330                        335                        340 | 1064 |
| atg ccc aca gaa gat gaa tac atg gac agg ccc tcc cag ccc aca gac<br>Met Pro Thr Glu Asp Glu Tyr Met Asp Arg Pro Ser Gln Pro Thr Asp<br>                345                        350                        355 | 1112 |
| cag tta ctg ttc ctc act gag cct gga agc aaa tcc aca cct cct ttc<br>Gln Leu Leu Phe Leu Thr Glu Pro Gly Ser Lys Ser Thr Pro Pro Phe<br>360                             365                         370 | 1160 |
| tct gaa ccc ctg gag gtg ggg gag aat gac agt tta agc cag tgc ttc<br>Ser Glu Pro Leu Glu Val Gly Glu Asn Asp Ser Leu Ser Gln Cys Phe<br>375                             380                         385                       390 | 1208 |
| acg ggg aca cag agc aca gtg ggt tca gaa agc tgc aac tgc act gag<br>Thr Gly Thr Gln Ser Thr Val Gly Ser Glu Ser Cys Asn Cys Thr Glu<br>                      395                        400                        405 | 1256 |
| ccc ctg tgc agg act gat tgg act ccc atg tcc tct gaa aac tac ttg<br>Pro Leu Cys Arg Thr Asp Trp Thr Pro Met Ser Ser Glu Asn Tyr Leu<br>                          410                        415                       420 | 1304 |
| caa aaa gag gtg gac agt ggc cat tgc ccg cac tgg gca gcc agc ccc<br>Gln Lys Glu Val Asp Ser Gly His Cys Pro His Trp Ala Ala Ser Pro<br>                      425                        430                        435 | 1352 |
| agc ccc aac tgg gca gat gtc tgc aca ggc tgc cgg aac cct cct ggg<br>Ser Pro Asn Trp Ala Asp Val Cys Thr Gly Cys Arg Asn Pro Pro Gly<br>                440                        445                        450 | 1400 |
| gag gac tgt gaa ccc ctc gtg ggt tcc cca aaa cgt gga ccc ttg ccc<br>Glu Asp Cys Glu Pro Leu Val Gly Ser Pro Lys Arg Gly Pro Leu Pro<br>455                             460                        465                       470 | 1448 |
| cag tgc gcc tat ggc atg ggc ctt ccc cct gaa gaa gaa gcc agc agg<br>Gln Cys Ala Tyr Gly Met Gly Leu Pro Pro Glu Glu Glu Ala Ser Arg<br>                          475                        480                        485 | 1496 |
| acg gag gcc aga gac cag ccc gag gat ggg gct gat ggg agg ctc cca<br>Thr Glu Ala Arg Asp Gln Pro Glu Asp Gly Ala Asp Gly Arg Leu Pro<br>                      490                        495                       500 | 1544 |
| agc tca gcg agg gca ggt gcc ggg tct gga agc tcc cct ggt ggc cag<br>Ser Ser Ala Arg Ala Gly Ala Gly Ser Gly Ser Ser Pro Gly Gly Gln<br>                          505                        510                        515 | 1592 |
| tcc cct gca tct gga aat gtg act gga aac agt aac tcc acg ttc atc<br>Ser Pro Ala Ser Gly Asn Val Thr Gly Asn Ser Asn Ser Thr Phe Ile<br>520                             525                         530 | 1640 |
| tcc agc ggg cag gtg atg aac ttc aag ggc gac atc atc gtg tcc tac<br>Ser Ser Gly Gln Val Met Asn Phe Lys Gly Asp Ile Ile Val Ser Tyr<br>535                             540                        545                       550 | 1688 |
| gtc agc cag acc tcg cag gag ggc gcg gcg gcg gct gcg gag ccc atg<br>Val Ser Gln Thr Ser Gln Glu Gly Ala Ala Ala Ala Ala Glu Pro Met<br>                          555                        560                        565 | 1736 |
| ggc cgc ccg gtg cag gag gag acc ctg gcg cgc cga gac tcc ttc gcg<br>Gly Arg Pro Val Gln Glu Glu Thr Leu Ala Arg Arg Asp Ser Phe Ala<br>                      570                        575                       580 | 1784 |
| ggg aac ggc ccg cgc ttc ccg gac ccg tgc ggc ggc ccc gag ggg ctg<br>Gly Asn Gly Pro Arg Phe Pro Asp Pro Cys Gly Gly Pro Glu Gly Leu<br>585                             590                        595 | 1832 |

```
cgg gag ccg gag aag gcc tcg agg ccg gtg cag gag caa ggc ggg gcc    1880
Arg Glu Pro Glu Lys Ala Ser Arg Pro Val Gln Glu Gln Gly Gly Ala
    600                 605                 610 aag gct tga gcgccccca tggctgggag cccgaagctc ggagccaggg              1929
Lys Ala
615 ctcgcgaggg cagcaccgca gcctctgccc cagccccggc cacccaggga tcgatcggta    1989
cagtcgagga agaccacccg gcattctctg cccactttgc cttccaggaa atgggctttt    2049
caggaagtga attgatgagg actgtcccca tgcccacgga tgctcagcag cccgccgcac    2109
tggggcagat gtctcccctg ccactcctca aactcgcagc agtaatttgt ggcactatga    2169
cagctatttt tatgactatc ctgttctgtg ggggggggg tctgttttcc ccccatattt     2229
gtattccttt tcataacttt tcttgatatc tttcctccct cttttttaat gtaaaggttt    2289
tctcaaaaat tctcctaaag gtgagggtct cttctttc tcttttcctt tttttttct      2349
ttttttggca acctggctct ggcccaggct agagtgcagt ggtgcgatta tagcccggtg    2409
cagcctctaa ctcctgggct caagcaatcc aagtgatcct cccacctcaa ccttcggagt    2469
agctgggatc acagctgcag gccacgccca gcttcctccc ccgactccc ccccagaga     2529
cacggtccca ccatgttacc cagcctggtc tcaaactccc cagctaaagc agtcctccag    2589
cctcggcctc ccaaagtact gggattacag gcgtgagccc ccacgctggc ctgctttacg    2649
tattttcttt tgtgcccctg ctcacagtgt tttagagatg gctttcccag tgtgtgttca    2709
ttgtaaacac ttttgggaaa gggctaaaca tgtgaggcct ggagatagtt gctaagttgc    2769
taggaacatg tggtgggact ttcatattct gaaaaatgtt ctatattctc attttttctaa   2829
aagaaagaaa aaaggaaacc cgatttattt ctcctgaatc tttttaagtt tgtgtcgttc    2889
cttaagcaga actaagctca gtatgtgacc ttacccgcta ggtggttaat ttatccatgc    2949
tggcagaggc actcaggtac ttggtaagca aatttctaaa actccaagtt gctgcagctt    3009
ggcattcttc ttattctaga ggtctctctg gaaagatgg agaaaatgaa caggacatgg     3069
ggctcctgga aagaagggc ccgggaagtt caaggaagaa taaagttgaa attttaaaaa    3129
aaaa                                                                 3133

<210> SEQ ID NO 4
<211> LENGTH: 616
<212> TYPE: PRT
<213> ORGANISM: Homo sapiens

<400> SEQUENCE: 4

Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Val Ala Gly Asn Ser Thr Thr Pro Arg Arg Cys
            100                 105                 110
```

```
Ala Cys Thr Ala Gly Tyr His Trp Ser Gln Asp Cys Glu Cys Cys Arg
            115                 120                 125
Arg Asn Thr Glu Cys Ala Pro Gly Leu Gly Ala Gln His Pro Leu Gln
        130                 135                 140
Leu Asn Lys Asp Thr Val Cys Lys Pro Cys Leu Ala Gly Tyr Phe Ser
145                 150                 155                 160
Asp Ala Phe Ser Ser Thr Asp Lys Cys Arg Pro Trp Thr Asn Cys Thr
                165                 170                 175
Phe Leu Gly Lys Arg Val Glu His His Gly Thr Glu Lys Ser Asp Ala
            180                 185                 190
Val Cys Ser Ser Ser Leu Pro Ala Arg Lys Pro Pro Asn Glu Pro His
        195                 200                 205
Val Tyr Leu Pro Gly Leu Ile Ile Leu Leu Leu Phe Ala Ser Val Ala
    210                 215                 220
Leu Val Ala Ala Ile Ile Phe Gly Val Cys Tyr Arg Lys Lys Gly Lys
225                 230                 235                 240
Ala Leu Thr Ala Asn Leu Trp His Trp Ile Asn Glu Ala Cys Gly Arg
                245                 250                 255
Leu Ser Gly Asp Lys Glu Ser Ser Gly Asp Ser Cys Val Ser Thr His
            260                 265                 270
Thr Ala Asn Phe Gly Gln Gln Gly Ala Cys Glu Gly Val Leu Leu Leu
        275                 280                 285
Thr Leu Glu Glu Lys Thr Phe Pro Glu Asp Met Cys Tyr Pro Asp Gln
    290                 295                 300
Gly Gly Val Cys Gln Gly Thr Cys Val Gly Gly Pro Tyr Ala Gln
305                 310                 315                 320
Gly Glu Asp Ala Arg Met Leu Ser Leu Val Ser Lys Thr Glu Ile Glu
                325                 330                 335
Glu Asp Ser Phe Arg Gln Met Pro Thr Glu Asp Glu Tyr Met Asp Arg
            340                 345                 350
Pro Ser Gln Pro Thr Asp Gln Leu Leu Phe Leu Thr Glu Pro Gly Ser
        355                 360                 365
Lys Ser Thr Pro Pro Phe Ser Glu Pro Leu Glu Val Gly Glu Asn Asp
    370                 375                 380
Ser Leu Ser Gln Cys Phe Thr Gly Thr Gln Ser Thr Val Gly Ser Glu
385                 390                 395                 400
Ser Cys Asn Cys Thr Glu Pro Leu Cys Arg Thr Asp Trp Thr Pro Met
                405                 410                 415
Ser Ser Glu Asn Tyr Leu Gln Lys Glu Val Asp Ser Gly His Cys Pro
            420                 425                 430
His Trp Ala Ala Ser Pro Ser Pro Asn Trp Ala Asp Val Cys Thr Gly
        435                 440                 445
Cys Arg Asn Pro Pro Gly Glu Asp Cys Glu Pro Leu Val Gly Ser Pro
    450                 455                 460
Lys Arg Gly Pro Leu Pro Gln Cys Ala Tyr Gly Met Gly Leu Pro Pro
465                 470                 475                 480
Glu Glu Glu Ala Ser Arg Thr Glu Ala Arg Asp Gln Pro Glu Asp Gly
                485                 490                 495
Ala Asp Gly Arg Leu Pro Ser Ser Ala Arg Ala Gly Ala Gly Ser Gly
            500                 505                 510
Ser Ser Pro Gly Gly Gln Ser Pro Ala Ser Gly Asn Val Thr Gly Asn
        515                 520                 525
```

```
Ser Asn Ser Thr Phe Ile Ser Ser Gly Gln Val Met Asn Phe Lys Gly
        530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
            595                 600                 605

Gln Glu Gln Gly Gly Ala Lys Ala
        610                 615

<210> SEQ ID NO 5
<211> LENGTH: 2291
<212> TYPE: DNA
<213> ORGANISM: Homo sapiens
<220> FEATURE:
<221> NAME/KEY: CDS
<222> LOCATION: (252)..(1457)

<400> SEQUENCE: 5
```

| | |
|---|---:|
| ctttccgccc cagccctgaa agcgttaacc ctggagcttt ctgcacaccc cccgaccgct | 60 |
| cccgcccaag cttcctaaaa agaaaggtg caaagtttgg tccaggatag aaaaatgact | 120 |
| gatcaaaggc aggcgatact tcctgttgcc gggacgctat atataacgtg atgagcgcac | 180 |
| gggctgcgga gacgcaccgg agcgctcgcc cagccgccgc ctccaagccc ctgaggtttc | 240 |

```
cggggaccac a atg aac aag ttg ctg tgc tgc gcg ctc gtg ttt ctg gac          290
            Met Asn Lys Leu Leu Cys Cys Ala Leu Val Phe Leu Asp
              1               5                  10 atc tcc att aag tgg acc acc cag gaa acg ttt cct cca aag tac ctt          338
Ile Ser Ile Lys Trp Thr Thr Gln Glu Thr Phe Pro Pro Lys Tyr Leu
         15                  20                  25 cat tat gac gaa gaa acc tct cat cag ctg ttg tgt gac aaa tgt cct          386
His Tyr Asp Glu Glu Thr Ser His Gln Leu Leu Cys Asp Lys Cys Pro
 30                  35                  40                  45 cct ggt acc tac cta aaa caa cac tgt aca gca aag tgg aag acc gtg          434
Pro Gly Thr Tyr Leu Lys Gln His Cys Thr Ala Lys Trp Lys Thr Val
                 50                  55                  60 tgc gcc cct tgc cct gac cac tac tac aca gac agc tgg cac acc agt          482
Cys Ala Pro Cys Pro Asp His Tyr Tyr Thr Asp Ser Trp His Thr Ser
             65                  70                  75 gac gag tgt cta tac tgc agc ccc gtg tgc aag gag ctg cag tac gtc          530
Asp Glu Cys Leu Tyr Cys Ser Pro Val Cys Lys Glu Leu Gln Tyr Val
         80                  85                  90 aag cag gag tgc aat cgc acc cac aac cgc gtg tgc gaa tgc aag gaa          578
Lys Gln Glu Cys Asn Arg Thr His Asn Arg Val Cys Glu Cys Lys Glu
 95                 100                 105 ggg cgc tac ctt gag ata gag ttc tgc ttg aaa cat agg agc tgc cct          626
Gly Arg Tyr Leu Glu Ile Glu Phe Cys Leu Lys His Arg Ser Cys Pro
110                 115                 120                 125 cct gga ttt gga gtg gtg caa gct gga acc cca gag cga aat aca gtt          674
Pro Gly Phe Gly Val Val Gln Ala Gly Thr Pro Glu Arg Asn Thr Val
                130                 135                 140 tgc aaa aga tgt cca gat ggg ttc ttc tca aat gag acg tca tct aaa          722
Cys Lys Arg Cys Pro Asp Gly Phe Phe Ser Asn Glu Thr Ser Ser Lys
            145                 150                 155 gca ccc tgt aga aaa cac aca aat tgc agt gtc ttt ggt ctc ctg cta          770
Ala Pro Cys Arg Lys His Thr Asn Cys Ser Val Phe Gly Leu Leu Leu
```

|  |  | 160 |  |  |  | 165 |  |  |  | 170 |  |  |  |  |
|---|---|---|---|---|---|---|---|---|---|---|---|---|---|---|
| act | cag | aaa | gga | aat | gca | aca | cac | gac | aac | ata | tgt | tcc | gga | aac | agt | 818 |
| Thr | Gln | Lys | Gly | Asn | Ala | Thr | His | Asp | Asn | Ile | Cys | Ser | Gly | Asn | Ser |  |
|  | 175 |  |  |  | 180 |  |  |  | 185 |  |  |  |  |  |  |

```
act cag aaa gga aat gca aca cac gac aac ata tgt tcc gga aac agt       818
Thr Gln Lys Gly Asn Ala Thr His Asp Asn Ile Cys Ser Gly Asn Ser
    175                 180                 185 gaa tca act caa aaa tgt gga ata gat gtt acc ctg tgt gag gag gca       866
Glu Ser Thr Gln Lys Cys Gly Ile Asp Val Thr Leu Cys Glu Glu Ala
190                 195                 200                 205 ttc ttc agg ttt gct gtt cct aca aag ttt acg cct aac tgg ctt agt       914
Phe Phe Arg Phe Ala Val Pro Thr Lys Phe Thr Pro Asn Trp Leu Ser
                210                 215                 220 gtc ttg gta gac aat ttg cct ggc acc aaa gta aac gca gag agt gta       962
Val Leu Val Asp Asn Leu Pro Gly Thr Lys Val Asn Ala Glu Ser Val
            225                 230                 235 gag agg ata aaa cgg caa cac agc tca caa gaa cag act ttc cag ctg      1010
Glu Arg Ile Lys Arg Gln His Ser Ser Gln Glu Gln Thr Phe Gln Leu
        240                 245                 250 ctg aag tta tgg aaa cat caa aac aaa gac caa gat ata gtc aag aag      1058
Leu Lys Leu Trp Lys His Gln Asn Lys Asp Gln Asp Ile Val Lys Lys
    255                 260                 265 atc atc caa gat att gac ctc tgt gaa aac agc gtg cag cgg cac att      1106
Ile Ile Gln Asp Ile Asp Leu Cys Glu Asn Ser Val Gln Arg His Ile
270                 275                 280                 285 gga cat gct aac ctc acc ttc gag cag ctt cgt agc ttg atg gaa agc      1154
Gly His Ala Asn Leu Thr Phe Glu Gln Leu Arg Ser Leu Met Glu Ser
                290                 295                 300 tta ccg gga aag aaa gtg gga gca gaa gac att gaa aaa aca ata aag      1202
Leu Pro Gly Lys Lys Val Gly Ala Glu Asp Ile Glu Lys Thr Ile Lys
            305                 310                 315 gca tgc aaa ccc agt gac cag atc ctg aag ctg ctc agt ttg tgg cga      1250
Ala Cys Lys Pro Ser Asp Gln Ile Leu Lys Leu Leu Ser Leu Trp Arg
        320                 325                 330 ata aaa aat ggc gac caa gac acc ttg aag ggc cta atg cac gca cta      1298
Ile Lys Asn Gly Asp Gln Asp Thr Leu Lys Gly Leu Met His Ala Leu
    335                 340                 345 aag cac tca aag acg tac cac ttt ccc aaa act gtc act cag agt cta      1346
Lys His Ser Lys Thr Tyr His Phe Pro Lys Thr Val Thr Gln Ser Leu
350                 355                 360                 365 aag aag acc atc agg ttc ctt cac agc ttc aca atg tac aaa ttg tat      1394
Lys Lys Thr Ile Arg Phe Leu His Ser Phe Thr Met Tyr Lys Leu Tyr
                370                 375                 380 cag aag tta ttt tta gaa atg ata ggt aac cag gtc caa tca gta aaa      1442
Gln Lys Leu Phe Leu Glu Met Ile Gly Asn Gln Val Gln Ser Val Lys
            385                 390                 395 ata agc tgc tta taa ctggaaatgg ccattgagct gtttcctcac aattggcgag      1497
Ile Ser Cys Leu
        400 atcccatgga tgagtaaact gtttctcagg cacttgaggc tttcagtgat atctttctca    1557 ttaccagtga ctaattttgc cacagggtac taaaagaaac tatgatgtgg agaaaggact    1617 aacatctcct ccaataaacc ccaaatggtt aatccaactg tcagatctgg atcgttatct    1677 actgactata ttttccctta ttactgcttg cagtaattca actggaaatt aaaaaaaaaa    1737 aactagactc cattgtgcct tactaaatat gggaatgtct aacttaaata gctttgagat    1797 ttcagctatg ctagaggctt ttattagaaa gccatatttt tttctgtaaa agttactaat    1857 atatctgtaa cactattaca gtattgctat ttatattcat tcagatataa gatttgtaca    1917 tattatcatc ctataaagaa acggtatgac ttaattttag aaagaaaatt atattctgtt    1977 tattatgaca aatgaaagag aaaatatata ttttttaatgg aaagtttgta gcattttcct   2037
```

```
aataggtact gccatatttt tctgtgtgga gtattttat aatttatct gtataagctg    2097 taatatcatt ttatagaaaa tgcattattt agtcaattgt ttaatgttgg aaaacatatg    2157
aaatataaat tatctgaata ttagatgctc tgagaaattg aatgtaccttt atttaaaaga   2217 ttttatggtt ttataactat ataaatgaca ttattaaagt tttcaaatta ttttttaaaa    2277
aaaaaaaaaa aaaa                                                      2291
```

<210> SEQ ID NO 6
<211> LENGTH: 401
<212> TYPE: PRT
<213> ORGANISM: Homo sapiens

<400> SEQUENCE: 6

```
Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320
```

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu

<210> SEQ ID NO 7
<211> LENGTH: 9
<212> TYPE: PRT
<213> ORGANISM: Artificial
<220> FEATURE:
<223> OTHER INFORMATION: Synthetic peptide
<220> FEATURE:
<223> OTHER INFORMATION: 2nd Cys is linked to 8th Cys through disulfide
      bond

<400> SEQUENCE: 7

Tyr Cys Trp Ser Gln Tyr Leu Cys Tyr
1               5

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
gatgacatta tctgtgaag                                                19

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
atctctgata tctccagg                                                 18

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
ctttgtgtgc ctttcaatcg                                               20

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11

```
gtgaggtaca gcctaccagt t                                                21
```

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12

```
aacttctttg ccaccggaga                                                  20
```

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13

```
ggtgcccttt ttacacgtga a                                                21
```

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14

```
caccatggag aaggccgggg                                                  20
```

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15

```
gacggacaca ttgggggtag                                                  20
```

<210> SEQ ID NO 16
<211> LENGTH: 8
<212> TYPE: PRT
<213> ORGANISM: Artificial
<220> FEATURE:
<223> OTHER INFORMATION: Tag sequence

<400> SEQUENCE: 16

Asp Tyr Lys Asp Asp Asp Asp Lys
1               5

<210> SEQ ID NO 17
<211> LENGTH: 8
<212> TYPE: PRT
<213> ORGANISM: Artificial
<220> FEATURE:
<223> OTHER INFORMATION: Tag sequence

<400> SEQUENCE: 17

Asp Tyr Leu Asp Asp Asp Asp Leu
1               5